United States Patent
Cossio Mora et al.

(10) Patent No.: US 7,638,550 B2
(45) Date of Patent: Dec. 29, 2009

(54) PYRROLIC DERIVATIVES WITH HISTONE DEACETYLASE INHIBITORY ACTIVITY

(75) Inventors: Fernando Pedro Cossio Mora, Leioa (ES); Manel Esteller Badosa, Madrid (ES); Aizpea Zubia Olascoaga, Leioa (ES); Dorleta Otaegui Ansa, Leioa (ES)

(73) Assignee: Universidad del Pais Vasco-Euskal Herriko Unibertsitatea (UPV-EHU) Fundacion Centro Nacional de Investigaciones Oncologicas Carlos III (CNIO) (ES)

( * ) Notice: Subject to any disclaimer, the term of this patent is extended or adjusted under 35 U.S.C. 154(b) by 656 days.

(21) Appl. No.: 10/571,497

(22) PCT Filed: Dec. 27, 2005

(86) PCT No.: PCT/ES2005/000708

§ 371 (c)(1),
(2), (4) Date: Mar. 10, 2006

(87) PCT Pub. No.: WO2007/074176

PCT Pub. Date: Jul. 5, 2007

(65) Prior Publication Data

US 2008/0262073 A1    Oct. 23, 2008

(51) Int. Cl.
*A61K 31/4025* (2006.01)
*C07D 333/10* (2006.01)
*C07D 295/00* (2006.01)

(52) U.S. Cl. .................. 514/422; 514/423; 548/517; 548/530

(58) Field of Classification Search ................ 514/422, 514/423; 548/517, 530
See application file for complete search history.

(56) References Cited

FOREIGN PATENT DOCUMENTS

| WO | WO 98/25896 | * | 6/1998 | ................ 548/200 |
|---|---|---|---|---|
| WO | WO 2004/103968 A | | 12/2004 | |
| WO | WO 2005/056004 | | 6/2005 | |

OTHER PUBLICATIONS

Extended European Search Report dated Sep. 14, 2009 relating to European Patent Application No. 05850516.5.
Mai et al., "3-(4-Aroyl-1-methyl-1H-2-pyrroly1)-N-hydroxy-2-propenamides as a New Class of Synthetic Histone Deacetylase Inhibitors. 2. Effect of Pyrrole-C2 and/or -C4 Substitutions on Biological Activity", J. Med. Chem. 2004, 47, pp. 1098-1109.
M. R. Graaf et al., "The risk of cancer in users of statins", Journal of Clinical Oncology, vol. 22, No. 12, 2004, pp. 2388-2394.
R.T. Morrison et al., "Organic Chemistry", Allyn and Bacon, Newton (Massachusetts, U.S.), XP002540604 Electrophilic Aromatic Substitution, p. 613.

* cited by examiner

*Primary Examiner*—Kamal A Saeed
*Assistant Examiner*—Samantha L Shterengarts
(74) *Attorney, Agent, or Firm*—Ostrolenk Faber LLP

(57) ABSTRACT

The invention describes new compounds derived from formula I pyrroles, methods for obtaining them and their application as drugs in pharmaceutical compositions for the treatment of cancer due to their inhibitory activity on certain histone deacetylases.

20 Claims, 7 Drawing Sheets

PYRROLIC DERIVATIVES WITH HISTONE DEACETYLASE INHIBITORY ACTIVITY

FIELD OF THE INVENTION

The invention is related to new compounds derived from pyrroles, with process for their preparation and with the use thereof as drugs for the treatment of cancer in pharmaceutical compositions due to their inhibitory action over certain histone diacetylases.

BACKGROUND OF THE INVENTION

The chemical synthesis of tri- and tetra-substituted pyrrole rings can be carried out in several ways using linear or convergent synthesis methodologies (Sundberg, in *Comprehensive Heterocyclic Chemistry*; Katrizki, A. and Rees, C. W. Eds.; Pergamon: Oxford, 1984; Vol. 4, p. 313). One sufficiently general way of preparation consists of the aromatisation of the substituted pyrrolidines (Fejes et al. *Tetrahedron* 2000, 56, 8545. Gupta et al. *Synth. Commun.* 1998, 28, 3151). The latter heterocyclics can, at their turn, be prepared in convergent form using cycloaddition between alkenes and azomethine ylides (Ayerbe et al. *J. Org. Chem.* 1998, 63, 1795. Vivanco et al. *J. Am. Chem. Soc.* 2000, 122, 6078). Coupling reactions of derivatives of carboxylic acids with hydroxylamine are also known to give rise to the formation of hydroxamic acids (Reddy et al. *Tetrahedron Lett.* 2000, 41, 6285) as well as reactions between substituted amines and phosgene and thiophosgene derivatives to produce, through the formation of intermediate isocyanates and thiocyanates, the corresponding N-hydroxyureas, N-hydroxythioureas, N-(alkyl) aminoureas and N-(alkyl) aminothioureas (Jain et al. *Bioorg. Med. Chem. Lett.* 2003, 13, 4223).

On the other hand, it is known that the inhibitors of histone deacetylases (HDACs) represent a promising way for the treatment of cancer, by means of blocking certain tumour growth mechanisms (McLaughin et al. *Biochem. Pharm.* 2004, 68, 1139. Krämer et al. *Trends Endocrin. Met.* 2001, 12, 294. Archer et al. *Curr. Opin. Genet. Dev.* 1999, 9, 171). Although the detailed mechanisms of therapeutic action of the aforementioned inhibitors are not well known, there is a general consensus in that the inhibition of the active centres of the HDACs facilitate the access of certain genes to transcription factors by the acetylation of histones localised in certain regions of the DNA which codes cell cycle control proteins such as the p21 cyclin dependent kinases (Archer et al. *Proc. Natl. Acad. Sci. USA* 1998, 95, 6791). Another advantage of this therapeutic target is that it is estimated that only about 2% of the transcription of DNA to mRNA is modulated by HDACs inhibitors (McLaughin et al. *Biochem. Pharm.* 2004, 68, 1139), which must have an effect on the low toxicity of these inhibitors, which has been observed in clinical trials (Van Lint et al. *Gen. Express* 1996, 5, 245. Glaser et al. *Mol. Cancer Ther.* 2003, 2, 151). Likewise, it is estimated that the clinical usefulness of HDACs inhibitors can increase on combining synergically with other treatments by improving the gene transcriptional profiles which make the development to resistances difficult (Keen et al. *Cancer Res. Treat.* 2003, 81, 177. Egger et al. *Nature* 2004, 429, 457).

Different families of HDACs inhibitors are known, whose general characteristics can be found in different reviews (Villar-Garea and Esteller *Int. J. Cancer* 2004, 112, 171 and *Curr. Drug Metab.* 2003, 4, 11. Grozinger et al. *Chem. Biol.* 2002, 9, 3. McLaughlin et al, *Drug Discov. Today* 2003, 8, 793. Monneret *Eur. J. Med. Chem.* 2005, 40, 1, Biel et al. *Angew. Chem. Int. Ed.* 2005, 44, 3186). In general terms, the structure of the most active inhibitors are characterised by having a cyclic or polycyclic part of a predominantly hydrophobic nature bound by a carbon spacer chain to a unit capable of being coordinated to the metal ion of the active centre of the HDAC. In particular, the synthesis of 3-(4-aroyl-1-methyl-1H-2-pyrrolyl)-N-hydroxy-2-propenamides has been described as inhibitors of HDAC (cf. Mai et al. *J. Med. Chem.* 2004, 47, 1098). In this case the spacer chain is unsaturated and positions 3 and 5 of the pyrrole ring are not substituted, resulting in a linear molecular geometry.

Despite the quantity of inhibitors obtained synthetically, their therapeutical usefulness is not free of problems, among them which must be mentioned are, the inhibition selectivity of different HDACs, some of which do not constitute useful therapeutic targets in oncology, toxicity, and chemical instability. In this context, the present invention describes a general method of synthesis of new HDAC inhibitors which incorporates the possibility of generating a wide variety of functional groups, which result in chemically stable molecules and with different polycyclic systems, spacer sizes, and coordinating units to the metal atom of the enzymes to inhibit.

The problem posed by the present invention is hence to provide compounds and compositions with a high selectivity in the inhibition of different HDACs related with the rising and development of neoplastic processes, with a high chemical stability and low toxicity. The solution proposed comprises the use of pyrrole derivatives of general formula I. These compounds have aryl or heteroaryl substituents in positions 3 and 5, as well as electron-attractor groups, such as the nitrate group in position 4, and heterogeneous groups in position 2 which consist of spacers of a different nature and the use of N-hydroxyurea, N-alkylamino(aryl)urea, N-hydroxythiourea and N-alkylamino(aryl)thiourea groups for coordinating to the metal ion of the HDACs. These pyrrole derivatives demonstrate a great capacity to inhibit cell proliferation and tumour growth.

In short, the present invention is intended to solve the existing need of having histone deacetylase inhibitors available having advantages such as, good pharmacological properties, stability in solid phase and in solution, the ease and efficiency of their chemical synthesis and the accessibility and variability of the starting chemical compounds.

OBJECT OF THE INVENTION

Figure 1:
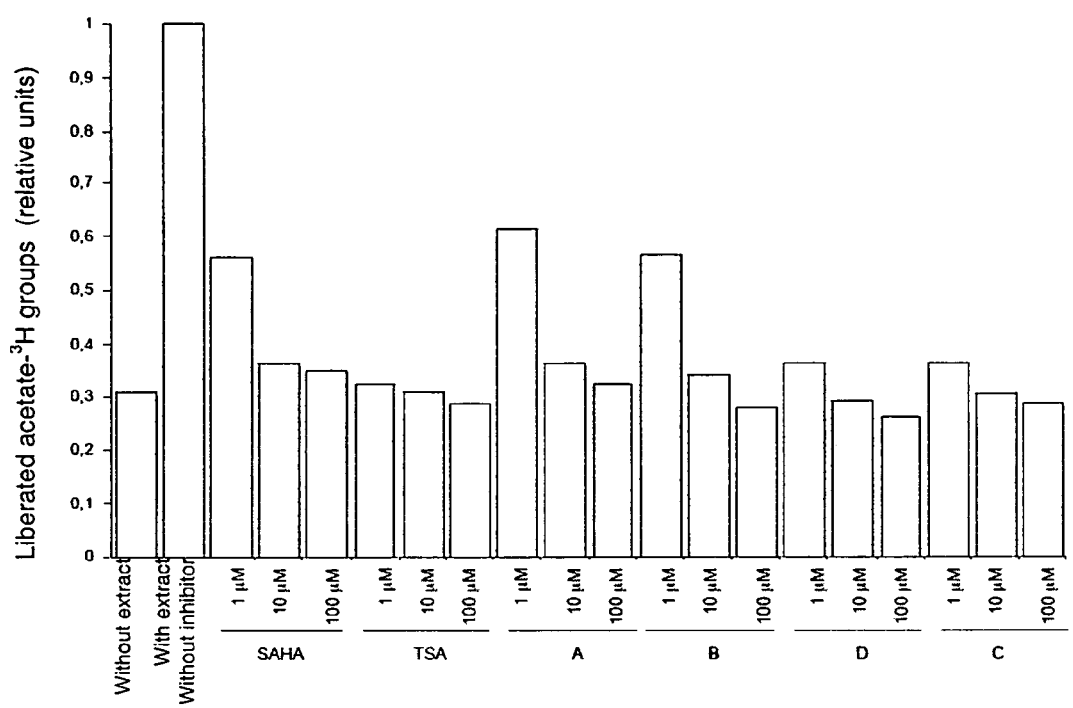
FIG. 1 shows the effect tested in vitro of some of the compounds object of the present invention on the deacetylase activity of histones of the cell line HCT116 (human colon carcinoma), compared with TSA (acronym for tricostatin A) and SAHA (acronym for suberoylanilide hydroxamic acid) used as a positive control.

The present invention has as an object the pyrrole derivatives of general formula I:

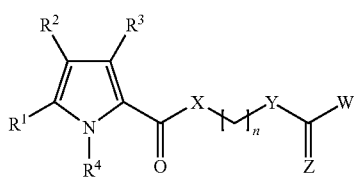

(I)

Likewise, another object of the present invention are the processes for preparing these compounds from general formula I.

Another additional object of the invention is the use of these derivatives for the treatment of different forms of cancer by restricting tumour growth through the inhibition of the action of certain histone deacetylases.

Lastly, this invention has as an object the preparation of a pharmaceutical composition which may include any pyrrole derivative from general formula I and at least one acceptable pharmaceutical excipient.

DETAILED DESCRIPTION OF THE INVENTION

Firstly, the present invention provides some compounds derived from pyrrole which have the following formula I:

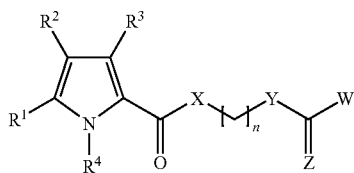

(I)

where:

$R^1$ and $R^3$ represent independently a phenyl radical; mono or polysubstituted phenyl in the different positions of the ring; or a C5-C10 heteroaryl group which contains at least one heteroatom of O, N or S;

$R^2$ represents a hydrogen atom or an electron-attractor group such as the nitro group; or an amine or amide group;

$R^4$ represents a hydrogen atom or a linear, branched or cyclic C1-C6 alkyl group;

(n) represents a number of methylene groups between 1 and 8, both inclusive;

(X) represents either a secondary amine group, an oxygen atom or a sulphur ion;

(Y) represents a group selected between methylene, substituted methylene and a secondary amine:

(Z) represents either an atom of oxygen or sulphur; and (W) represents a group selected between hydroxyl, hydroxyamine, hydrazine and alkyl, aryl or heteroaryl-hydrazine.

In a preferred embodiment the compounds of general formula I are:

6-(3,5-diphenyl-1H-pyrrole-2-carboxamide) hexanoic acid, with the following structural formula:

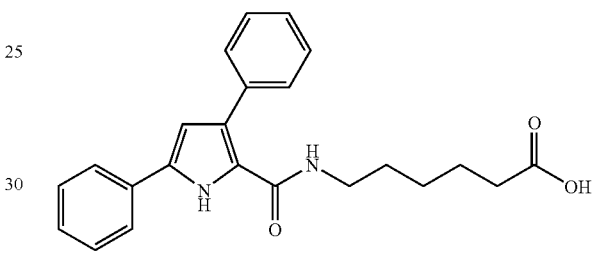

6-(4-nitro-3,5-diphenyl-1H-pyrrole-2-carboxamide) hexanoic acid, with the following structural formula:

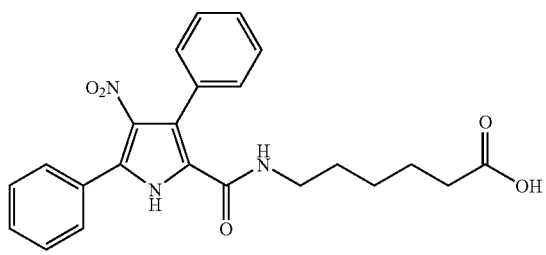

N-(5-(Hydroxycarbamoyl)pentyl)-3-phenyl-5-(4-methoxyphenyl)-1H-pyrrole-2-carboxamide, with the following structural formula:

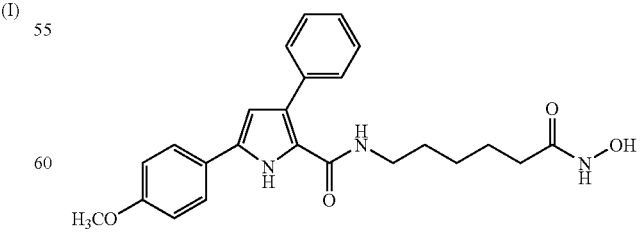

N-(5-(Hydroxycarbamoyl)pentyl)-5-phenyl-3-(4-methoxyphenyl)-1H-pyrrole-2-carboxamide, with the following structural formula:

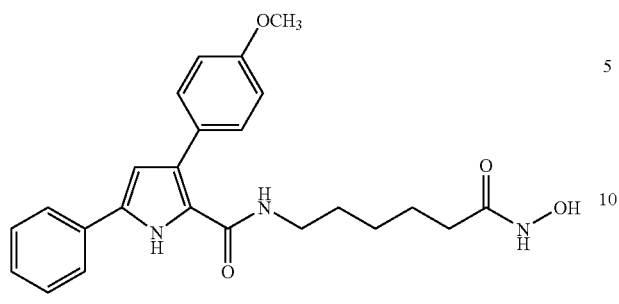

N-(5-(Hydroxycarbamoyl)pentyl)-3-phenyl-5-(4-methoxyphenyl)-4-nitro-1H-pyrrole-2-carboxamide, with the following structural formula

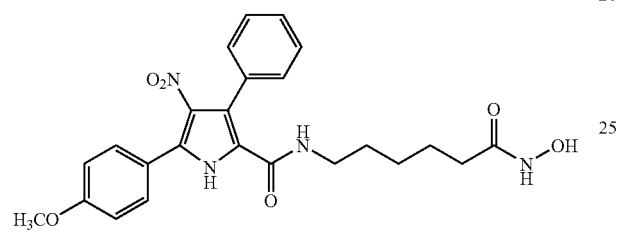

1-(4-(3,5-bis(3,5-Dimethoxyphenyl)-1H-pyrrole-2-carboxamide)butyl)-3-hydroxyurea, with the following structural formula:

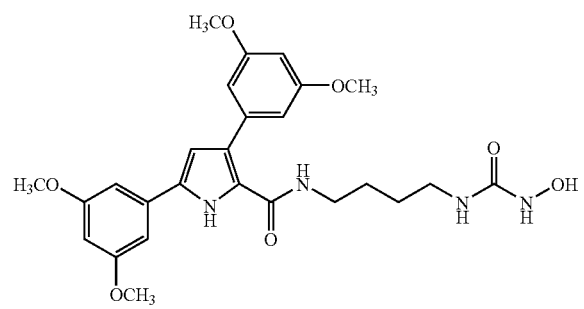

1-(4-(5-(4-Methoxyphenyl)-4-nitro-3-(thiophene-2-yl)-1H-pyrrole-2-carboxamide)butyl)-3-(2-methylamino)urea, with the following structural formula:

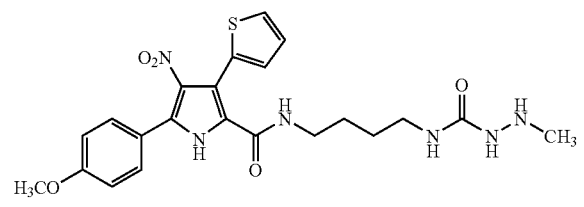

Another aspect of the invention makes reference to different processes for obtaining the compounds of general formula I. The following methods A to E describe the processes for obtaining the compounds of general formula (Ia), (Ib), (Ic) and (Id) as we will see next. These compounds (Ia) to (Id) are compounds whose general formula falls within general formula I.

Method A

Method A represents a process for the preparation of compounds of general formula (Ia):

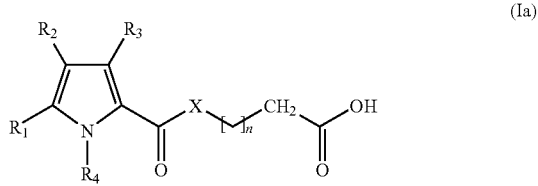

(Ia)

where $R_1$, $R_2$, $R_3$, $R_4$, X and n have the significance given previously, which comprises the reaction of a mixture made up of:

a) 1H-pyrrole-2-carboxylic acid of formula II,

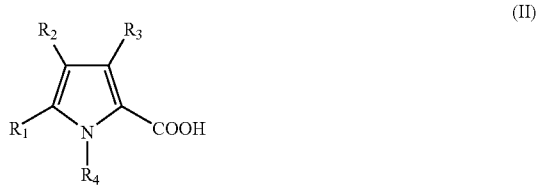

(II)

b) A compound of formula III,

(III)

where $R^5$ is an alkoxycarbonyl, c) A reagent for the activation of the carboxyl group; and
d) A tertiary amine, selected among the cyclic or acyclic aliphatics with C3-C10 carbons and the alkano-aromatics with C9-C15 carbons, and make the product obtained react with a mixture of lithium or sodium hydroxide, dimethoxyethane and water.

For the aims of the invention, the reaction mixture, made up of the four compounds of phases a) to d) can be made by adding one of the components to the mixture before the other three in an organic solvent and at a temperature of −85° C. to +25° C., preferably temperatures near 0° C. Next it is left for a time to complete the reaction, while reaching ambient temperature. Once the coupling reaction is completed, the ester obtained after following the general method is made to react with the mixture of lithium or sodium hydroxide, dimethoxyethane and water, thus yielding, after the corresponding treatment, the compounds of general formula (Ia).

Method B

Method B represents a process for the preparation of compounds of the general formula (Ib):

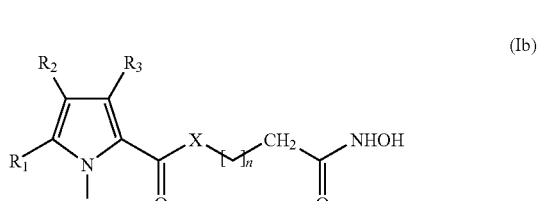

(Ib)

where $R_1$, $R_2$, $R_3$, $R_4$, X and n have the significance given previously, which comprises the reaction of a mixture made up of:

a) A 1H-pyrrole-2-carboxylic acid of formula II,

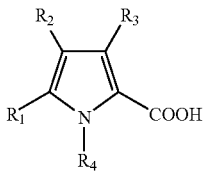
(II)

b) A compound of formula III,

HX—(CH$_2$)$_n$—R$^5$     (III)

where R$^5$ is an alkoxycarbonyl, c) A reagent for the activation of the carboxyl group; and d) A tertiary amine, selected among the cyclic or acyclic aliphatics with C3-C10 carbons and the alkano-aromatics with C9-C15 carbons, and to add the resulting product over a mixture of hydroxylamine hydrochloride and phenolphthalein in the presence of an excess of sodium methoxide in methanol.

For the aims of the invention, the reaction mixture made up of the four compounds of phases a) to d) can be made by adding one of the components to the mixture before the other three in an organic solvent and at a temperature of −85° C. to +25° C., preferably temperatures near 0° C. Next it is left for a time to complete the reaction, while reaching ambient temperature. Once the coupling reaction is completed, the ester obtained is added over a mixture of hydroxylamine hydrochloride and phenolphthalein in the presence of an excess of sodium methoxide in methanol. Once the reaction is completed, after the corresponding treatment, the compounds of general formula (1b) are obtained.

Method C

Method C represents a process for the preparation of compounds from general formula (Ic):

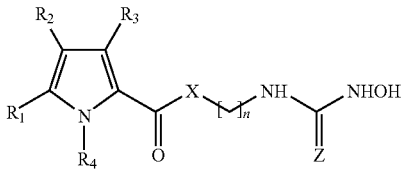
(Ic)

where R$_1$, R$_2$, R$_3$, R$_4$, X, Z and n have the significance given previously, which comprises the reaction of a mixture made up of:

a) A 1H-pyrrole-2-carboxylic acid of formula II,

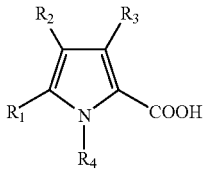
(II)

b) A compound of formula III,

HX—(CH$_2$)$_n$—R$^5$     (III)

where R$^5$ is t-butoxycarbamoyl (NHBoc) or benzyloxycarbamoyl (NHCBz), c) A reagent for the activation of the carboxyl group; and d) A tertiary amine, selected among the cyclic or acyclic aliphatics with C3-C10 carbons and the alkano-aromatics with C9-C15 carbons.

to unprotect the product obtained using acid treatment or hydrolysis and making it react with phosgene or its analogues such as diphosgene, triphosgene or thiophosgene, obtaining an isocyanate or a thio-isocyanate which is treated with hydroxylamine.

For the aims of the invention, the reaction mixture formed by the four compounds of phases a) to d) can be made up by adding one of the components to the mixture before the other three in an organic solvent and at a temperature of −85° C. to +25° C., preferably temperatures near 0° C. Next, it is left for a time to complete the reaction, while reaching ambient temperature. Depending on the significance of R$_5$ in compound III, that is, depending on whether R$_5$ represents t-butoxycarbamoyl (NHBoc) or benzyloxycarbamoyl (NHCBz), the subsequent treatments will be different. In the case where R$_5$ is NHBoc the resulting product must be subjected to an acid treatment preferably in a reaction at ambient temperature with trifluoroacetic acid in a halogenated solvent. When R$_5$ represents NHCBz the resulting product is subjected to hydrogenolysis, preferably by a reaction with hydrogen gas or ammonium formate in a short chain alcohol as solvent and in the presence of a palladium heterogenic catalyst. In both cases, after the unprotection, a primary amine is obtained which is treated with phosgene or one of its derivatives such as diphosgene or triphosgene or also thiophosgene. When the reaction is with phosgene, diphosgene or triphosgene, the final compound (Ic) will have an atom of oxygen at Z. If on the other hand the treatment is with thiophosgene Z will be a sulphur atom.

After the reaction either with phosgene (diphosgene, triphosgene) or thiophosgene the corresponding isocyanates or thio-isocyanates are obtained which are treated in situ with hydroxylamine for obtaining the compounds of formula (Ic).

Method D

Method D represents a process for the preparation of compounds of general formula (Id):

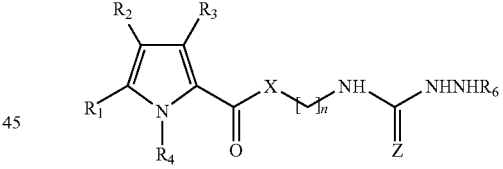
(Id)

where R$_1$, R$_2$, R$_3$, R$_4$, X, Z and n have the significance given previously and R$_6$ is an H, C1-C6 alkyl, aryl or heteroaryl of 5 or 6 members with 1 or more heteroatoms selected between O, N or S, which comprises the reaction of a mixture made up of:

a) A 1H-pyrrole-2-carboxylic acid of formula II,

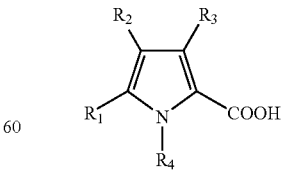
(II)

b) A compound of formula III,

HX—(CH$_2$)$_n$—R$^5$     (III)

where R$^5$ is t-butoxycarbamoyl (NHBoc) or benzyloxycarbamoyl (NHCBz), c) A reagent for the activation of the carboxyl group; and
d) A tertiary amine, selected among the cyclic or acyclic aliphatics with C3-C10 carbons and the alkano-aromatics with C9-C15 carbons, to unprotect the product obtained by means of acid treatment or hydrolysis and making it react with phosgene or its analogues such as diphosgene, triphosgene or thiophosgene, obtaining an isocyanate or a thio-isocyanate which is treated with hydrazine or alkyl, aryl or heteroaryl hydrazines.

For the aims of the invention, the reaction mixture formed by the four compounds of phases a) to d) can be made up by adding one of the components to the mixture before the other three in an organic solvent and at a temperature of −85° C. to +25° C., preferably temperatures near 0° C. Next, it is left for a time to complete the reaction, while reaching ambient temperature. Depending on the significance of $R_5$ in compound III, that is, depending on whether $R_5$ represents t-benzyloxycarbamoyl (NHBoc) or benzyloxycarbamoyl (NHCBz), the subsequent treatments will be different. In the case where $R_5$ is NHBoc the resulting product must be subjected to an acid treatment preferably in the reaction at ambient temperature with trifluoroacetic acid in a halogenated solvent. When $R_5$ represents NHCBz the resulting product is subjected to hydrogenolysis, preferably by a reaction with the hydrogen gas or ammonium formiate in a short chain alcohol as solvent and in the presence of a palladium heterogenic catalyst. In both cases, after the unprotection, a primary amine is obtained which is treated with phosgene or one of its derivatives such as diphosgene or triphosgene or also thiophosgene. When the reaction is with phosgene, diphosgene or triphosgene, the final compound (Ic) will have an atom of oxygen at Z. If on the other hand the treatment is with thiophosgene Z will be a sulphur atom.

After the reaction either with phosgene (diphosgene, triphosgene) or thiophosgene the corresponding isocyanates or thio-isocyanates are obtained which are treated in situ with hydrazines or alkylhydrazines to give the compounds of formula (Id).

Method E

Method E represents an additional process for the preparation of compounds of general formula (Id):

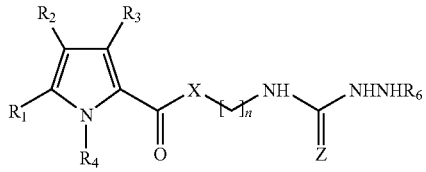

(Id)

where $R_1$, $R_2$, $R_3$, $R_4$, X, Z and n have the significance given previously and $R_6$ is an H, C1-C6 alkyl, aryl or heteroaryl of 5 or 6 members with 1 or more heteroatoms selected between O, N or S, which comprises the reaction of a mixture made up of:
a) A 1H-pyrrole-2-carboxylic acid of formula II,

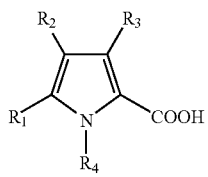

(II)

b) A compound of formula III, $$HX\text{—}(CH_2)_n\text{—}R^5 \qquad (III)$$

where $R^5$ is 3-benzyloxyureyl or 3-alkyl, aryl or heteroaryl ureyl,
c) A reagent for the activation of the carboxyl group; and
d) A tertiary amine, selected among the cyclic or acyclic aliphatics with C3-C10 carbons and the alkane aromatics with C9-C15 carbons, If the coupling reaction detailed previously is carried out with N-benzyloxyureas or thioureas, it is only necessary to liberate the corresponding N-hydroxyureas or thioureas by means of hydrogenolysis in the presence of an appropriate catalyst. In the case of the N-alkyl(aryl,heteroaryl)aminoureas or thioureas, if the said radicals are already introduced in the corresponding precursors (III), the coupling reaction yields the expected final molecules directly.

As a common element of methods A-E, The carboxyl group activation reagent is preferably phenyl dichlorophosphate, diethyl phosphorocyamidate (DEPC) or the system formed by 1-hydroxybenzotriazole and N-(3-dimethylaminopropyl)-N'-ethylcarbodiimide.

A tertiary amine, for its part, is a reagent common to methods A and B, selected from the cyclic or acyclic aliphatics with C3-C10 carbons and the alkano-aromatics with C9-C15 carbons. This tertiary amine is preferably selected from N-methyl pyrrolidine or N-methylmorpholine.

Also it is preferable to carry out the reaction between the elements a) to d) of each one of the methods A to E using irradiation with microwaves.

The preparation of the previously mentioned compounds of formula II is carried out in an organic solvent or in the absence of it and irradiation with microwaves, making react, in first place, a mixture comprising:
a) A nitroalkene of (E) or (Z) configuration with the following formula IV, $$O_2N\text{—}CH\text{=}CH\text{—}R^3 \qquad (IV)$$

where:
$R^3$ has the significance given previously;
b) An imine of (E) or (Z) configuration with the following formula V, $$R^1\text{—}CH\text{=}N\text{—}CH_2\text{—}COOR^6 \qquad (V)$$

where:
$R^1$ has the significance given previously, and
$R^6$ represents a C1-C6 alkyl or aryl group;
c) A metal salt, preferably selected from lithium perchlorate, silver perchlorate or silver acetate, and
d) A tertiary organic base, selected from the cyclic or acyclic aliphatics with C3-C10 carbons or the alkano-aromatics with C9-C15 carbons.

For the aims of the invention, the reaction mixture made up of the four components indicated above can be carried out using irradiation with microwaves or by adding one of the components over the other three, in an organic solvent and at a temperature between −25° C. to +25° C., preferably at temperatures near to +25° C. Once the cyclo-addition reaction is completed a mixture of 2-alkoxycarbonyl pyrrolidines, corresponding to the substituents selected for each particular reaction, are obtained. This mixture is dissolved in a cyclic ether such as tetrahydrofuran or a high boiling point acyclic one such as bis(2-methoxyethyl) ether, also known as "diglyme" and an oxidising agent is added such as manganese dioxide, hydrogen peroxide or 2,3-dichloro-5,6-dicyano-1,4-benzoquinone. After a certain time at temperatures between +60° C. and +250° C., a mixture made up of 2-alkoxycarbonyl-NH-pyrrole and the corresponding 2-alkoxycarbonyl-4-nitro-NH-pyrrole is obtained, whose components can be separated by fractionated crystallisation or chromatography. The acids of general formula II are obtained by means of alkaline hydrolysis of the previous esters, preferably by treating them with lithium or sodium hydroxide in a mixture of water and dimethoxyethane.

An additional aspect of this invention refers to the use of these compounds of general formula I for the treatment of cancer. The mechanism of action of these compounds is due to their antagonistic properties with histone deacetylases involved in the blocking of the synthesis of proteins responsible for regulation processes such as apoptosis or growth and cell proliferation. These properties prevent or block the binding of the deacetylases and related enzymatic complexes to its natural substrates, such as the residues of lysine N-acetylated in the ε position of the terminal lysines of the histones, therefore these remain in the mono- or poly-acetylated state.

A final aspect of the invention refers to a composition which consists of at least one of the compounds of general formula I and one or more acceptable pharmaceutical excipients. The formula I compounds of the present invention can be administered as a pure substance as well as in the form of pharmaceutical formulations, although the administration of the compound in combined form is preferred. The combination of the medication is preferably in the form of a formulation which:

i) Only contains the formula I compound;
ii) Contains one or more excipients and or transporter substances; and
iii) May contain any additional therapeutically active substance.

The excipients, transporter substances and auxiliary substances must be pharmaceutically and pharmacologically tolerable, in such a way that they may be combined with other components of the formulation or preparation and not produce adverse effects in the treated organism.

The formulations include those which are appropriate for oral or parenteral administration (including subcutaneous, intradermal, intramuscular and intravenous), although the best administration route will depend on the state of the patient.

The formulations can be in simple dose form and prepared according to known methods in the pharmacology field. The quantities of active substances to administer may vary depending on the characteristics of the therapy, although they will generally vary between 1 mg and 500 mg per day in one or several doses.

To help understand the preceding ideas better, some working examples of the present invention are described below. These examples are merely illustrative.

Example 1

Preparation of 5-phenyl-3-(4-methoxyphenyl)-1H-pyrrole-2-carboxylic acid, with the following structural formula

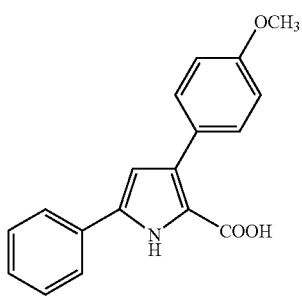

and 5-phenyl-3-(4-methoxyphenyl)-4-nitro-1H-pyrrole-2-carboxylic acid with the following structural formula

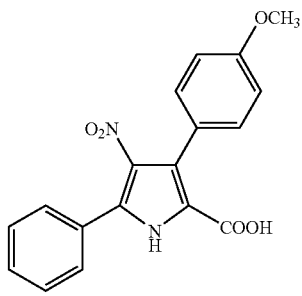

To a mixture of methyl N-phenylmethylidene glycinate (14.17 g, 80.0 mmol) in acetonitrile (800 ml), triethylamine (12 ml, 80.0 mmol), silver acetate (1.98 g, 11.9 mmol) and (E)-2-(4-methoxyphenyl)-1-nitroethene (14.33 g, 80.0 mmol) were added in succession. The progress of the reaction was followed by thin layer chromatography. Once the reaction was completed, the mixture was filtered through a Celite bed and washed with saturated $NH_4Cl$ solution (2×150 ml) and with water (2×150 ml). Once dried over $MgSO_4$, the solution was evaporated under reduced pressure, obtaining 26.5 g of a mixture of diastereomers of 5-phenyl1-3-(4-methoxyphenyl)-2-methoxycarbonyl-4-nitropyrrolidine. 12.22 g (34.27 mmol) of this mixture was dissolved in bis(2-methoxyethyl) ether (343 ml) under inert atmosphere and manganese dioxide, (29.8 g, 343 mmol), was added. The reaction mixture was refluxed with stirring for 48 h. After this time, the mixture was brought to ambient temperature and filtered through a Celite bed. The solution obtained was concentrated at reduced pressure, 7.93 g of a mixture consisting of 5-phenyl-3-(4-methoxyphenyl)-2-methoxycarbonyl-4-nitro-1H-pyrrole and 5-phenyl-3-(4-methoxyphenyl)-2-methoxycarbonyl-1H-pyrrole being obtained. The products were separated using flash column chromatography, and each of them were hydrolysed separately as shown next. 10% NaOH (40 ml, aqueous solution) was added drop wise to a solution of the corresponding ester (4.0 mmol) in ethanol (100 ml), and the mixture was stirred under reflux. The progress of the reaction was followed by thin layer chromatography. Once the reaction was completed, the mixture was cooled to 0° C., neutralised with 1N HCl and extracted with methylene chloride (3×50 ml). The combined organic fractions were dried over $MgSO_4$ and evaporated under reduced pressure, the corresponding carboxylic acid being obtained.

5-phenyl-3-(4-methoxyphenyl)-2-methoxycarbonyl-1H-pyrrole-2-carboxylic acid:

Yield, 41%; m.p. 198° C. (dec.); IR 3467, 1643 $cm^{-1}$; $^1$H-NMR (δ ppm, DMSO-$d_6$) 11.72 (s, 1H), 7.88 (d, 2H, J=7.7 Hz), 7.51 (d, 2H, J=8.4 Hz), 7.38 (t, 2H, J=7.6 Hz), 7.26 (t, 1H, J=7.2 Hz), 6.91 (d, 2H, J=8.4 Hz), 6.69 (s, 1H), 3.78 (s, 3H), 3.34 (b s, 1H); $^{13}$C-NMR (δ ppm, DMSO-$d_6$) 162.5, 157.9, 134.4, 131.3, 131.2, 130.3, 128.6, 127.9, 127.0, 125.1, 119.8, 113.0, 112.9, 109.3, 55.0, 54.9; Anal. Calc. for $C_{18}H_{15}NO_3$: C, 73.71; H, 5.15; N, 4.78. Found: C, 73.56; H, 5.08; N, 4.81%.

5-phenyl-3-(4-methoxyphenyl)-4-nitro-1H-pyrrole-2-carboxylic acid:

Yield, 28%; m.p. 190° C.; IR 3437, 1663, 1493 $cm^{-1}$; $^1$H-NMR (δ ppm, DMSO-$d_6$) 7.57-7.52 (m, 2H), 7.48-7.43

(m, 3H), 7.24 (d, 2H, J=8.4 Hz), 6.90 (d, 2H, J=8.4 Hz), 3.79 (s, 3H); $^{13}$C-NMR (δ ppm, DMSO-d$_6$) $^{13}$C-NMR (δ ppm, DMSO-d$_6$) 161.6, 158.3, 133.5, 132.5, 131.1, 129.3, 129.0, 128.0, 124.5, 124.2, 121.1, 112.7, 54.9; Anal. Calc. for C$_{18}$H$_{14}$N$_2$O$_5$: C, 63.90; H, 4.17; N, 8.28. Found: C, 63.85; H, 4.20; N, 8.27%.

Example 2

Preparation of 3-phenyl-5-(4-methoxyphenyl)-1H-pyrrole-2-carboxylic acid, with the following structural formula

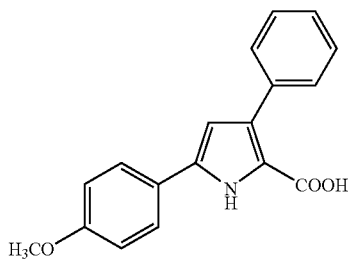

and 3-phenyl-5-(4-methoxyphenyl)-4-nitro-1H-pyrrole-2-carboxylic acid, with the following structural formula

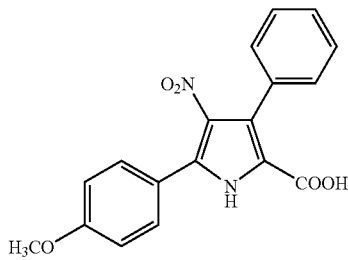

These materials were prepared using a method substantially similar to that of Example 1, the compounds of the title being obtained as yellow solids.

3-phenyl-5-(4-methoxyphenyl)-1H-pyrrole-2-carboxylic acid: Yield, 52%; m.p. 251° C.; IR 3457, 3316, 1618 cm$^{-1}$; $^1$H-NMR (δ ppm, DMSO-d$_6$) 10.67 (b s, 1H), 7.88 (d, 2H, J=7.5 Hz), 7.70 (d, 2H, J=8.5 Hz), 7.23 (t, 2H, J=7.5 Hz), 7.11 (t, 1H, J=7.3 Hz), 6.87 (d, 2H, J=8.5 Hz), 6.52 (s, 1H), 3.74 (s, 3H), 3.38 (b s, 1H); $^{13}$C-NMR (δ ppm, DMSO-d$_6$) 166.1, 157.5, 137.1, 129.7, 128.9, 127.9, 126.9, 125.3, 125.2, 124.7, 113.9, 106.4, 54.9; Anal. Calcd. for C$_{18}$H$_{15}$NO$_3$: C, 73.71; H, 5.15; N, 4.78. Found: C, 73.48; H, 5.11; N, 4.79%.

3-phenyl-5-(4-methoxyphenyl)-4-nitro-1H-pyrrole-2-carboxylic acid: Yield 35%; m.p. 106-107° C.; IR 3407, 1668, 1507, 1351 cm$^{-1}$; $^1$H-NMR (δ ppm, CDCl$_3$) 9.32 (s, 1H), 7.54 (d, 2H, J=8.6 Hz), 7.42-7.38 (m, 5H), 7.01 (d, 2H, J=8.6 Hz), 3.88 (s, 3H); $^{13}$C-NMR (δ ppm, CDCl$_3$) 163.4, 161.1, 135.2, 133.2, 130.8, 130.3, 129.7, 128.7, 128.2, 127.8, 127.6, 120.6, 114.3, 114.2, 55.4; Anal. Calc. for C$_{18}$H$_{14}$N$_2$O$_5$: C, 63.90; H, 4.17; N, 8.28. Found: C, 63.77; H, 4.19; N, 8.30%.

Example 3

Preparation of 5-(4-methoxyphenyl)-3-(thiophene-2-yl)-1H-pyrrole-2-carboxylic acid, with the following structural formula

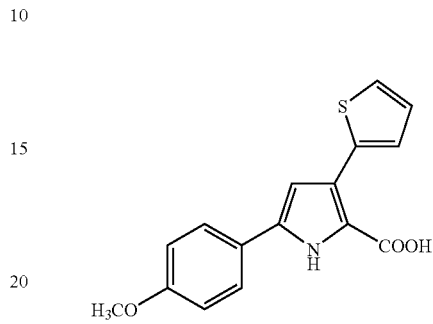

and 5-(4-methoxyphenyl)-4-nitro-3-(thiophene-2-yl)-1H-pyrrole-2-carboxylic acid, with the following structural formula

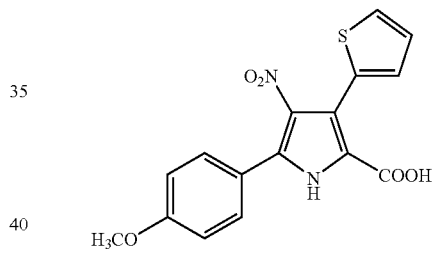

These materials were prepared using a method substantially similar to that of Example 1, the compounds of the title being obtained as yellow solids.

5-(4-methoxyphenyl)-3-(thiophene-2-yl)-1H-pyrrole-2-carboxylic acid: Yield, 54%; m.p. 153-154° C.; IR 3424, 3112, 2964, 1610 cm$^{-1}$; $^1$H-NMR (δ ppm, CDCl$_3$) 8.29, (b s, 1H), 7.41 (d, 2H, J=8.6 Hz), 7.10 (d, 1H, J=5.0 Hz), 7.07 (d, 1H, J=3.1 Hz), 7.02-6.98 (m, 2H), 6.92 (d, 2H, J=8.6 Hz), 6.58 (s, 1H), 3.82 (s, 3H); $^{13}$C-NMR (δ ppm, CDCl$_3$) 158.6, 139.2, 133.0, 127.4, 125.3, 121.8, 121.2, 120.4, 114.9, 114.4, 103.5, 71.9, 70.5, 59.0, 55.3; Anal. Calc. for C$_{16}$H$_{13}$NO$_3$S: C, 64.20; H, 4.38; N, 4.68. Found: C, 64.11; H, 4.35; N, 4.70%.

5-(4-methoxyphenyl)-4-nitro-3-(thiophene-2-yl)-1H-pyrrole-2-carboxylic acid: Yield, 28%; m.p. 180-181° C.; IR 3408, 3120, 1610, 1511 cm$^{-1}$; $^1$H-NMR (δ ppm, DMSO-d$_6$) 7.54 (d$_a$, 1H, J=3.4 Hz), 7.49 (d, 2H, J=8.3 Hz), 7.03 (b s, 2H), 7.00 (d, 2H, J=8.2 Hz), 3.81 (s, 3H); $^{13}$C-NMR (δ ppm, DMSO-d$_6$) $^{13}$C-NMR (δ ppm, DMSO-d$_6$) 161.1, 135.1, 133.7, 130.1, 129.3, 127.3, 126.8, 120.1, 114.3, 65.9, 55.4, 15.2; Anal. Calc. for C$_{16}$H$_{12}$N$_2$O$_5$S: C, 55.81; H, 3.51; N, 8.14. Found: C, 56.09; H, 3.49; N, 8.14%.

Example 4

Preparation of 6-(3,5-diphenyl-1H-pyrrole-2-carboxamide)hexanoic acid, with the following structural formula

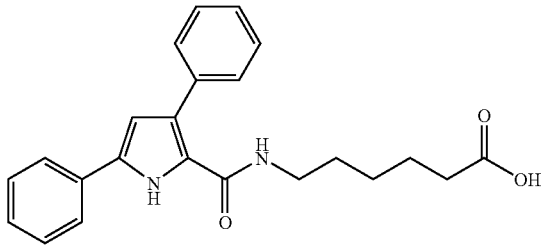

A solution of 3,5-diphenyl-1H-pyrrole-2-carboxylic acid (0.39 g, 1.5 mmol) and chlorohydrate of the methyl ester of 6-aminohexanoic acid (0.25 g, 1.5 mmol) in DMF (7.5 ml) was cooled to 0° C. Triethylamine (1.15 ml, 8.25 mol), 1-hydroxybenzotriazole (0.22 g, 1.65 mmol), chlorohydrate of N-(3-dimethylaminopropyl)-N'-ethylcarbodiimide (0.32 g, 1.65 mmol) and N-methylmorpholine (0.165 ml, 1.5 mmol) were added in succession, and the mixture was stirred at 0° C. for 2 h, and for another 96 hours at ambient temperature. After this time, ethyl acetate (300 ml) was added, and the solution obtained was washed with water (90 ml), 1 N $Na_2S_2O_3$ (90 ml, aqueous solution), water (90 ml), $NaHCO_3$ (90 ml, saturated aqueous solution), and NaCl (90 ml, saturated aqueous solution), dried over $MgSO_4$ and evaporated under reduced pressure, with 0.47 g (1.2 mmol) of ester being obtained.

The methyl ester obtained was dissolved in ethylene glycol dimethyl ether (6 ml) and the solution was cooled to 0° C. Next, a solution of 1 N LiOH (3.6 ml) was added drop wise and the resulting mixture was stirred at 0° C. The progress of the reaction was monitored by thin layer chromatography. Once the reaction was completed, 3.6 ml of an aqueous solution of 10% citric acid (pH≈6) was added. The solution was extracted with methylene chloride (3×5 ml), and the combined organic fractions were dried over $MgSO_4$ and evaporated under reduced pressure. The crude reaction product was ground in diethyl ether to give 0.42 g of a white solid.

Yield, 74%; m.p. 228-229° C.; IR 3427, 3246, 1608 cm$^{-1}$; $^1$H-NMR (δ ppm, DMSO-d$_6$) 13.05 (s, 1H), 8.73 (s, 1H), 7.99 (d, 2H, J=7.7 Hz), 7.52 (d, 2H, J=7.5 Hz), 7.36-7.29 (m, 4H), 7.21 (dd, 2H, J=12.5 Hz, J'=7.0 Hz), 6.65 (s, 1H), 3.21 (dd, 2H, J=11.3 Hz, J'=5.6 Hz), 2.05 (t, 2H, J=6.6 Hz), 1.54-1.44 (m, 4H), 1.36-1.30 (m, 2H); $^{13}$C-NMR (δ ppm, DMSO-d$_6$) 177.5, 160.8, 136.1, 132.7, 131.8, 129.0, 128.5, 128.3, 127.6, 126.5, 125.9, 124.6, 123.3, 108.3, 37.3, 28.8, 26.6, 25.5; Anal. Calc. for $C_{23}H_{24}N_2O_3$: C, 73.38; H, 6.43; N, 7.44. Found: C, 73.45; H, 6.41; N, 7.44%.

Example 5

Preparation of 6-(4-nitro-3,5-diphenyl-1H-pyrrole-2-carboxamide)hexanoic acid, with the following structural formula

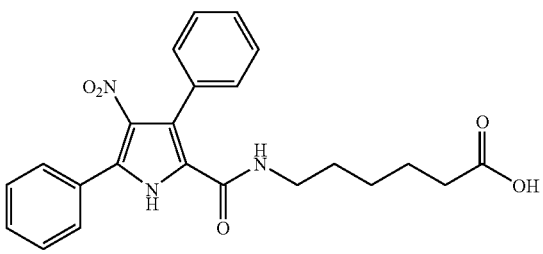

This material was prepared using a method substantially similar to that of Example 4, the compound of the title being obtained as yellow solid.

Yield, 71%; m.p. 153-154° C.; IR 3417, 3155, 1638, 1492 cm$^{-1}$; $^1$H-NMR (δ ppm, DMSO-d$_6$) 7.58 (d, 2H, J=7.2 Hz), 7.36 (t, 2H, J=7.2 Hz), 7.32-7.23 (m, 7H), 4.87 (b s, 2H), 3.07 (dd, 2H, J=12.9 Hz, J'=6.6 Hz), 2.09 (t, 2H, J=7.3 Hz), 1.46-1.40 (m, 2H), 1.35-1.29 (m, 2H), 1.18-1.12 (m, 2H); $^{13}$C-NMR (δ ppm, DMSO-d$_6$) 176.0, 161.9, 136.8, 134.4, 133.4, 131.8, 130.1, 129.0, 127.5, 127.4, 127.3, 126.3, 122.8, 71.0, 64.8, 57.9, 38.2, 35.0, 28.8, 26.0, 24.7, 15.1; Anal. Calc. for $C_{23}H_{23}N_3O_5$: C, 65.55; H, 5.50; N, 9.97. Found: C, 65.37; H, 5.44; N, 10.01%.

Example 6

Preparation of N-(5-(hydroxycarbamoyl)pentyl-3-phenyl-S-(4-methoxyphenyl)-1H-pyrrole-2-carboxamide, with the following structural formula

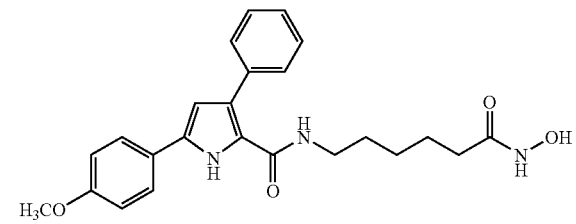

To a solution of hydroxylamine chlorohydrate (0.26 g, 3.75 mmol) and phenolphthalein (1 mg) in methanol (1.25 ml) under inert atmosphere, an aliquot of sodium methoxide in methanol (taken from a solution of 0.65 g, 12.0 mmol of sodium methoxide in 3.3 ml of methanol under inert atmosphere) is added drop wise until a permanent pink colour is observed in the solution. Methyl-6-(3-phenyl-5-(4-methoxyphenyl)-1H-pyrrole-2-carboxamide)hexanoate (0.53 g, 1.25 mmol), prepared from 3-phenyl-5-(4-methoxyphenyl)-1H-pyrrole-2-carboxylic acid and the chlorohydrate of the methyl ester of 6-aminohexanoic acid according to the method in Example 4, and sodium methoxide in methanol (5.0 mmol, 1.4 ml of a solution prepared earlier) were added in succession. The mixture was stirred for 26 h, the formation of a dense precipitate being observed. After this time, water (3 ml) is added to the reaction mixture. This solution was acidified with glacial acetic acid and extracted with methylene chloride (3×10 ml). The combined organic fractions were dried over $MgSO_4$ and evaporated under reduced pressure, 0.46 g of the product of the title being obtained as a white solid.

Yield, 87%; m.p. 157-158° C.; IR 3407, 3226, 1663, 1608 cm$^{-1}$; $^1$H-NMR (δ ppm, DMSO-d$_6$) 11.44 (s, 1H), 10.34 (s, 1H), 8.66 (s, 1H), 7.73 (d, 2H, J=7.8 Hz), 7.49 (d, 2H, J=7.7 Hz), 7.36 (t, 2H, J=7.3 Hz), 7.30 (t$_a$, 1H, J=5.1 Hz), 7.26 (t, 2H, J=7.3 Hz), 6.97 (d, 2H, J=7.9 Hz), 6.56 (s, 1H), 3.78 (s, 3H), 3.16 (dd, 2H, J=12.0 Hz, J'=5.9 Hz), 1.93 (t, 2H, J=7.2 Hz), 1.51-1.45 (m, 2H), 1.43-1.38 (m, 2H), 1.24-1.17 (m, 2H); $^{13}$C-NMR (δ ppm, DMSO-d$_6$) 168.9, 160.9, 158.2, 135.7, 132.8, 128.7, 127.9, 127.3, 126.2, 125.9, 124.3, 122.7, 114.0, 107.1, 55.1, 32.1, 28.7, 26.0, 24.8; Anal. Calc. for C$_{24}$H$_{27}$N$_3$O$_4$: C, 68.39; H, 6.46; N, 9.97. Found: C, 68.25; H, 6.42; N, 9.98%.

Example 7

Preparation N-(5-(hydroxycarbamoyl)pentyl-3-phenyl-5-(4-methoxyphenyl)-4-nitro-1H-pyrrole-2-carboxamide, with the following structural formula

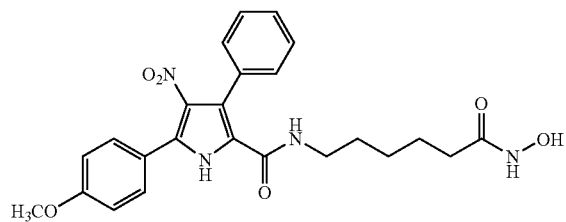

This material was prepared using a method substantially similar to that of Example 6, the compound of the title being obtained as a yellow coloured solid.

Yield, 84%; m.p. 126-127° C.; IR 3397, 3185, 1668, 1628, 1507, 1356 cm$^{-1}$; $^1$H-NMR (δ ppm, DMSO-d$_6$) 12.59 (b s, 1H), 10.33 (s, 1H), 8.66 (s, 1H), 7.53 (d, 2H, J=8.5 Hz), 7.44-7.39 (m, 3H), 7.35 (d, 2H, J=7.0 Hz), 7.03 (d, 2H, J=8.5 Hz), 6.71 (t$_a$, 1H, J=4.4 Hz), 3.82 (s, 3H), 3.03 (dd, 2H, J=11.9 Hz, J'=6.0 Hz), 1.88 (t, 2H, J=7.3 Hz), 1.40-1.34 (m, 2H), 1.24-1.18 (m, 2H), 1.03-0.96 (m, 2H); $^{13}$C-NMR (δ ppm, DMSO-d$_6$) 168.9, 159.9, 159.4, 133.3, 132.0, 131.1, 130.9, 129.9, 128.0, 127.6, 123.3, 121.4, 121.1, 113.5, 55.2, 32.0, 28.4, 25.7, 24.7; Anal. Calc. for C$_{24}$H$_{26}$N$_4$O$_6$: C, 61.79; H, 5.62; N, 12.01. Found: C, 61.71; H, 5.59; N, 12.04%.

With the purpose of making the ideas expressed in these last examples easier to understand, the different stages of synthesis leading to the compounds of the previous examples are shown in Scheme 1, which is included below,

SCHEME 1

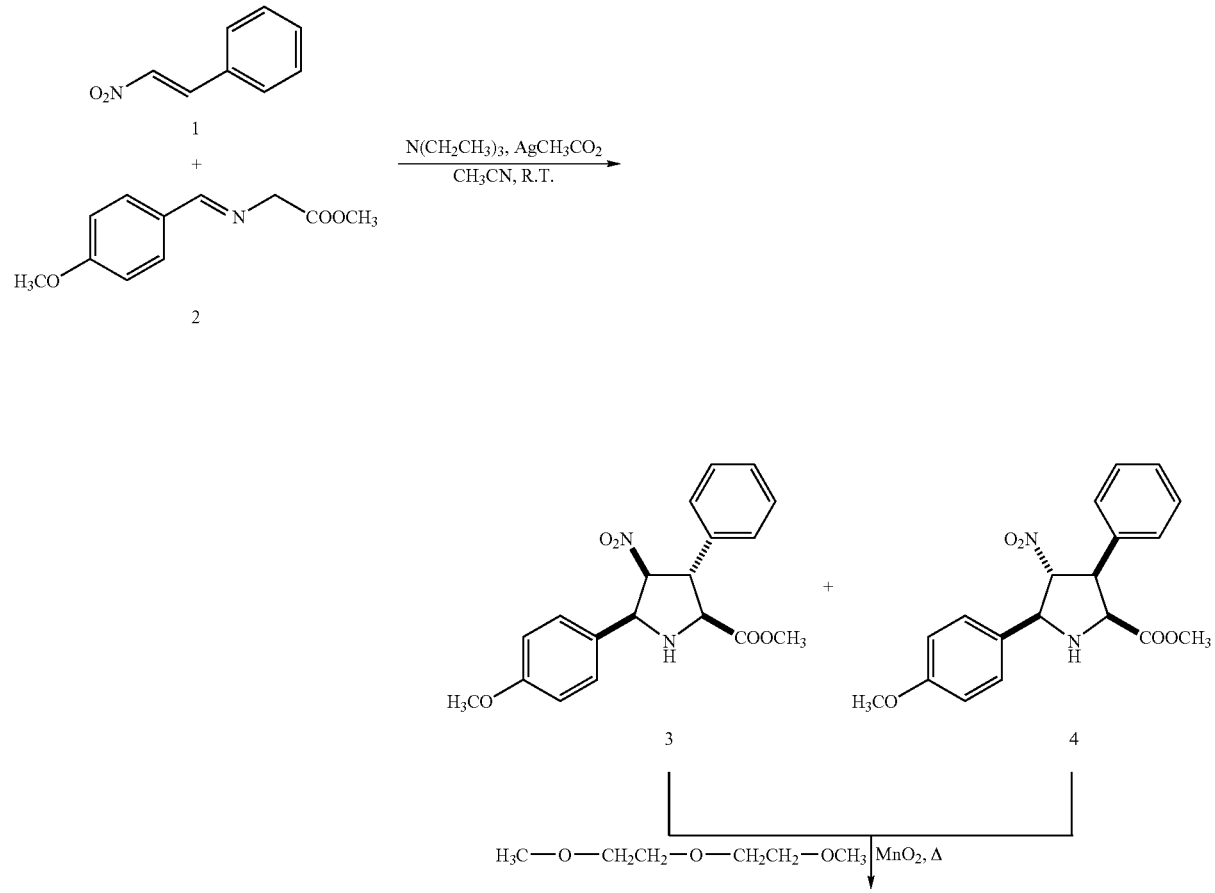

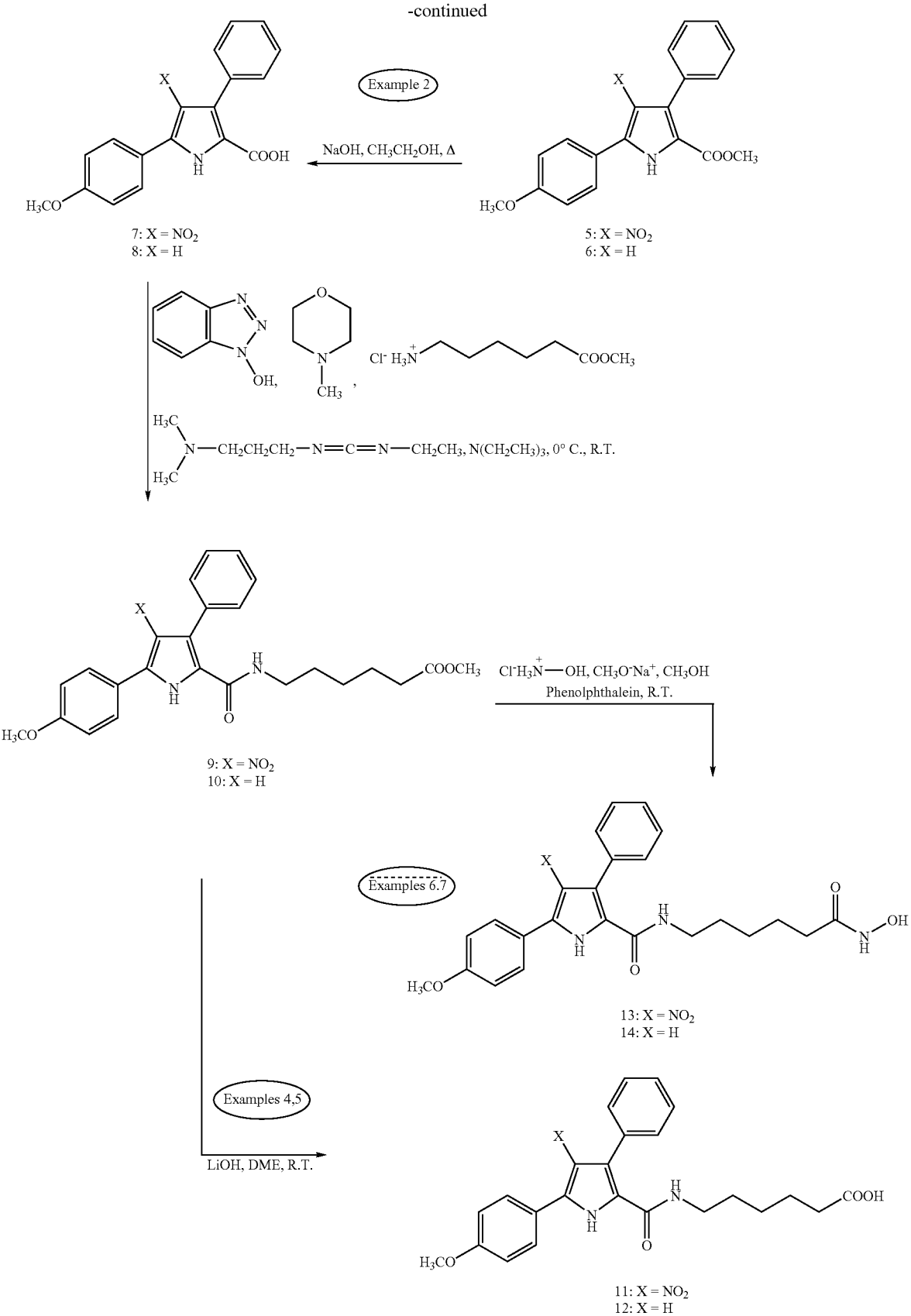

Example 8

Preparation of N-(5-(hydroxycarbamoyl)pentyl-3-(4-methoxyphenyl)-5-phenyl 1H-pyrrole-2-carboxamide, with the following structural formula

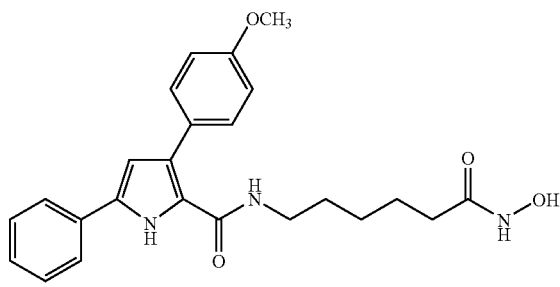

This material was prepared using a method substantially similar to that of Example 6, the compound of the title being obtained as pale yellow coloured solid. Yield, 80%; m.p. 142° C.; IR 3417, 3256, 1663, 1613, 1547, 1306 cm$^{-1}$; $^1$H-NMR (δ ppm, DMSO-d$_6$) 12.59 (b s, 1H), 10.33 (s, 1H), 8.66 (s, 1H), 7.53 (d, 2H, J=8.5 Hz), 7.44-7.39 (m, 3H), 7.35 (d, 2H, J=7.0 Hz), 7.03 (d, 2H, J=8.5 Hz), 6.71 (t$_a$, 1H, J=4.4 Hz), 3.82 (s, 3H), 3.03 (dd, 2H, J=12.43 Hz, J'=6.35 Hz), 1.94 (t, 2H, J=7.3 Hz), 1.54-1.45 (m, 2H), 1.45-1.37 (m, 2H), 1.28-1.16 (m, 2H); $^{13}$C-NMR (δ ppm, DMSO-d$_6$) 169.0, 161.0, 158.0, 132.6, 131.6, 129.9, 128.6, 127.8, 127.2, 126.6, 124.5, 123.1, 113.4, 108.1, 55.0, 32.2, 28.8, 26.1, 24.9. Anal. Calc. for C$_{24}$H$_{27}$N$_3$O$_4$: C, 68.39; H, 6.46; N, 9.97. Found: C, 68.27; H, 6.43; N, 9.99%.

Example 9

Preparation of N-(5-(hydroxycarbamoyl)pentyl-3-(4-methoxyphenyl)-5-(4-methoxyphenyl)-4-nitro-1H-pyrrole-2-carboxamide, with the following structural formula

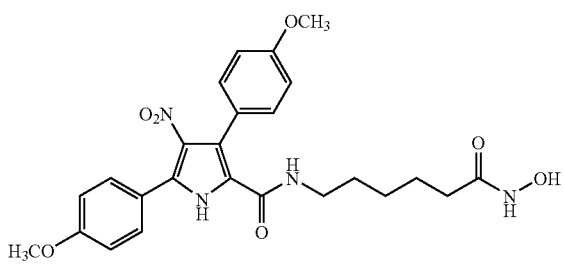

This material was prepared using a method substantially similar to that of Example 6, the compound of the title being obtained as pale yellow coloured solid. Yield, 94%; m.p. 155° C.; IR 3397, 3155, 1638, 1497, 1356 cm$^{-1}$; $^1$H-NMR (δ ppm, DMSO-d$_6$) 11.59 (s, 1H), 10.34 (s, 1H), 8.68 (s, 1H), 7.63-7.53 (m, 2H,), 7.52-7.41 (m, 3H), 7.29 (d, 2H, J=8.5 Hz), 6.99 (d, 2H, J=8.5 Hz), 6.72 (t$_a$, 1H, J=4.4 Hz), 3.80 (s, 3H), 3.05 (dd, 2H, J=12.02 Hz, J'=6.24 Hz), 1.89 (t, 2H, J=7.3 Hz), 1.50-1.33 (m, 2H), 1.33-1.16 (m, 2H), 1.14-0.98 (m, 2H); $^{13}$C-NMR (δ ppm, DMSO-d$_6$). 168.9, 159.4, 158.8, 133.0, 131.6, 131.2, 129.3, 129.1, 129.0, 128.0, 123.5, 121.0, 113.5, 55.0, 32.0, 28.3, 25.7, 24.6 Anal. Calc. for C$_{24}$H$_{26}$N$_4$O$_6$: C, 61.79; H, 5.62; N, 12.01. Found: C, 61.40; H, 5.77; N, 11.80%.

Example 10

Preparation of 4-(4-aminobutyl)-1-methylsemicarbazide, with the following structural formula

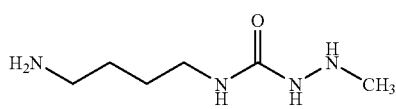

A mixture of di-tert-butyl dicarbonate (10.9 g, 51 mmol) in methanol (30 ml) was added drop wise on to a solution of 1,4-diaminobutane (11.12 g, 150 mmol) in triethylamine (30 ml, 215 mmol) and methanol (300 ml). The resulting mixture was stirred at ambient temperature for 16 h. After this time, the triethylamine and methanol were evaporated under reduced pressure. The resulting oil was dissolved in methylene chloride (100 ml) and washed with 10% sodium carbonate (2×50 ml, aqueous solution). The organic phase was dried over MgSO$_4$ and evaporated under reduced pressure. So was obtained the monoprotected amine (7.8 g, 41.42 mmol).

To a solution of the monoprotected amine (6 g, 31.86 mmol) and triphosgene (3.48 g, 11.72 mmol) in methylene chloride (438 ml) a solution of sodium bicarbonate (18.23 g, 63.72 mmol) in water (438 ml) is added drop wise at ambient temperature. The resulting biphasic system was vigorously stirred for 1.5 h. After this time the organic phase was decanted, dried over MgSO$_4$ and evaporated at reduced pressure. The resulting oil (4.3 g, 20 mmol) was dissolved in methanol (6.8 ml) and was added slowly drop wise at 0+ C. onto another previously prepared solution of methyl hydrazine (1.1 ml, 20.8 mmol) and water (4.05 ml). The mixture was stirred for 45 minutes at 0+ C. After this time the precipitate was filtered and 3.492 g of a white coloured solid was obtained whose spectroscopic properties were judged compatible with 4-(4-tert-butoxycarbonylaminobutyl)-1-methylsemicarbazide.

Another solution, trifluoroacetic acid (4.96 ml, 44 mmol) in methylene chloride (22 ml) was added slowly over 30 minutes to a solution (0.500 g, 1.92 mmol) of the previously obtained precipitate in methylene chloride (27.5 ml) at 0° C. The mixture was stirred for 2 hours. After this time toluene (50 ml) was added and it was evaporated at reduced pressure until half the volume, repeating the process several times. In this way, the trifluoroacetate of the ammonium salt (0.720 g, 2.63 mmol) of the compound of the title was obtained.

Yield, 68%; IR 3387, 3115, 1673 cm$^{-1}$; $^1$H-NMR (δ ppm, DMSO-d$_6$) 7.88 (s, 3H), 7.42-7.15 (m, 2H), 3.78-3.64 (m, 1H), 3.58 (s, 3H), 3.16-2.97 (m, 2H), 2.95-2.73 (m, 2H), 1.80-1.38 (m, 4H); $^{13}$C-NMR (δ ppm, DMSO-d$_6$) 159.0, 158.6, 158.1, 157.7, 156.7, 51.1, 26.3, 24.3.

Example 11

Preparation de la 1-(4-(5-(4-methoxyphenyl)-4-nitro-3-(thiophene-2-yl)-1H-pyrrole-2-carboxamide)butyl)-3-(2-methylamine)urea, with the following structural formula

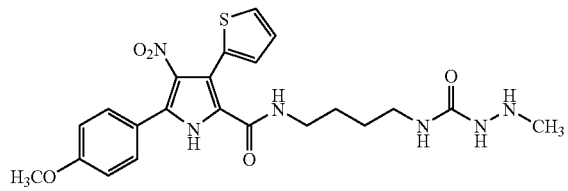

A solution of 5-(4-methoxyphenyl)-4-nitro-3-(thiophene-2-yl)-1H-pyrrole-2-carboxylic acid (0.434 g, 1.25 mmol) and trifluoroacetate of the ammonium salt of 4-(4-aminobutyl)-1-methylsemicarbazide (0.345 g, 1.25 mmol) in DMF (6.25 ml) was cooled to a 0° C. Next, triethylamine (0.98 ml, 7.04 mmol), 1-hydroxybenzotriazole (0.210 g, 1.37 mmol), N-(3-dimethylaminopropyl)-N'-ethylcarbodiimide chlorohydrate (0.263 g, 1.37 mmol) and N-methylmorpholine (0.14 ml, 1.25 mmol) were added in succession. The resulting mixture was stirred for 2 h at 0° C., and for another 96 hours at ambient temperature. After this time, ethyl acetate (250 ml) was added, and the solution obtained was washed with water (80 ml), 1 N $Na_2S_2O_3$ (80 ml, aqueous solution), water (80 ml), $NaHCO_3$ (80 ml, saturated aqueous solution), and NaCl (80 ml, saturated aqueous solution), dried over $MgSO_4$ and evaporated under reduced pressure, 0.400 g (0.82 mmol) of the compound of the title being obtained.

Yield, 65.6%; m.p. 185-187° C.; IR 3408, 3161, 1639, 1511 $cm^{-1}$; $^1$H-NMR (δ ppm, $CDCl_3$): 10.4 (s, 1H), 7.56 (dd, 1H, J=5.5 Hz, J'=0.8), 7.54 (d, 2H, J=8.7 Hz), 7.20-7.15 (m, 3H), 6.98 (d, 2H, J=8.7 Hz), 5.74 (t, 1H, J=5.2 Hz), 4.66 (s, 1H), 3.86 (s, 4H), 3.67 (s, 3H), 3.13-3.04 (m, 4H), 1.31-1.24 (m, 4H); $^{13}$C-NMR (δ ppm, $CDCl_3$): 160.7, 159.6, 157.0, 134.6, 132.9, 131.5, 130.9, 129.5, 128.7, 127.6, 123.2, 121.1, 113.9, 113.7, 55.4, 52.1, 40.5, 38.7, 27.0, 26.2. Calculated molecular ion for $C_{22}H_{26}N_6O_5S$: m/z 486.14. Found: 471.1 ($M^+$—Me).

Example 12

Preparation of 1-(4-aminomethyl)-3-(benzyloxy)urea, with the following structural formula

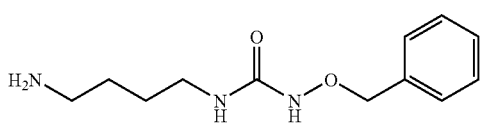

This material was prepared using a method substantially similar to that of Example 10, using benzyloxyamine in place of methylhidrazine. After the addition-unprotection sequence previously specified, the compound of the title was obtained as the trifluoroacetate of the corresponding ammonium salt.

Yield, 68%; IR 3759, 3356, 1648 $cm^{-1}$; $^1$H-NMR (δ ppm, DMSO-$d_6$) 7.82 (s, 3H), 7.52-7.28 (m, 7H), 5.00 (s, 2H), 3.09-2.92 (m, 2H), 2.90-2.68 (m, 2H), 1.68-1.32 (m, 4H); $^{13}$C-NMR (δ ppm, DMSO-$d_6$) 159.6, 158.2, 157.7, 136.4, 128.5, 128.1, 127.8, 77.2, 38.0, 26.6, 24.3, 24.0. Calculated molecular ion for $C_{13}H_{20}N_3O_2$: m/z 237.32. Found 238.0.

Example 13

Preparation of 1-(4-(3,5-bis(3,5-Dimethoxyphenyl)-1H-pyrrole-2-carboxamide)butyl)-3-(benzyloxy)urea, with the following structural formula

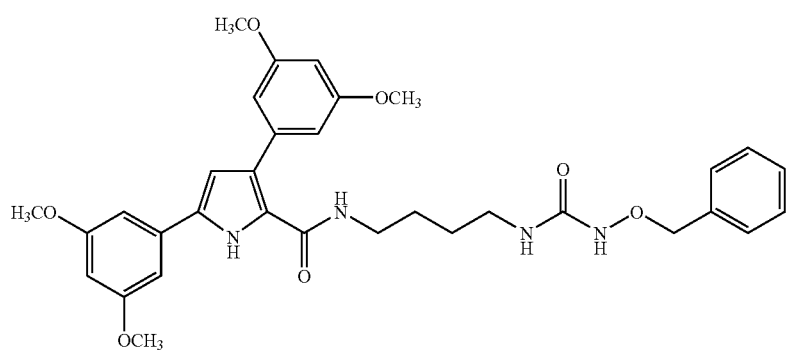

This material was prepared using a method substantially similar to that of Example 11, from 3,5-bis(3,5-dimethoxyphenyl)-1H-pyrrole carboxylic acid and the trifluoroacetate of the ammonium salt of 1-(4-aminomethyl)-3-(benzyloxy)urea.

Yield, 81%; IR 3407, 3216, 1688, 1597 $cm^-$; $^1$H-NMR (δ ppm, CDCl3) 9.87 (s, 1H), 7.44-7.32 (m, 5H), 7.13 (s, 1H), 6.77 (d, 2H, J=2.0 Hz), 6.62 (d, 2H, J=2.2 Hz), 6.50 (d, 2H, J=2.6 Hz), 6.43 (t, 1H, J=2.0 Hz), 6.03 (t, 1H, J=5.5 Hz), 5.62 (t, 1H, J=5.3 Hz), 4.80 (s, 2H), 3.85 (s, 6H), 3.82 (s, 6H), 3.28 (dd, 2H, J=11.9 Hz, J'=5.9 Hz), 3.15 (dd, 2H, J=12.7 Hz, J'=6.5 Hz), 1.41-1.29 (m, 4H); $^{13}$C-NMR (δ ppm, CDCl3) 161.2, 160.0, 137.6, 135.4, 134.1, 133.2, 130.8, 129.2, 128.8, 128.7, 127.7, 122.2, 110.0, 107.4, 103.0, 100.0, 99.8, 78.6, 72.3, 10.1, 68.1, 55.4, 39.1, 38.8, 27.1, 26.6. Molecular ion calculated for $C_{33}H_{38}N_4O_7$; m/z 602.68. Found: 603.2.

Example 14

Preparation of 1-(4-(3,5-bis(3,5-Dimethoxyphenyl)-1H-pyrrole-2-carboxamide)butyl)-3-hydroxyurea, with the following structural formula

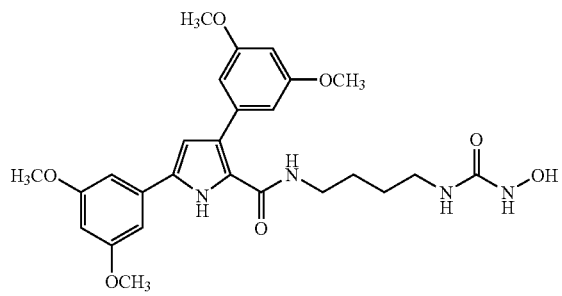

A solution of 1-(4-(3,5-bis(3,5-dimethoxyphenyl)-1H-pyrrole-2-carboxamide)butyl)-3-(benzyloxy)urea (0.200 g, 0.33 mmol) in ethyl acetate (66 ml) and ethanol (16.5 ml) was prepared, to which the catalyst, 10% Pd—C (0.116 g, 0.11 mmol), was added. The mixture was stirred at ambient temperature with a flow of hydrogen for 5 hours. After this time, the resulting suspension was filtered over celite and the filtrate was evaporated under reduced pressure. In this way, the product of the title was obtained as a colourless oil.

Yield, 71%; IR 3416, 3244, 2948, 1598 cm$^{-1}$; $^1$H-NMR (δ ppm CDCl$_3$) 10.3 (s, 1H), 6.78 (s, 2H), 6.60 (d, 2H, J=1.7 Hz), 6.53-6.44 (m, 2H), 6.39 (s, 1H), 6.17-6.02 (m, 1H), 4.81 (s, 1H), 3.86-3.78 (m, 13H), 3.34-3.16 (m, 4H), 1.48-1.33 (m, 4H); $^{13}$C-NMR (δ ppm, CDCl$_3$) 161.2, 137.6, 134.6, 134.5, 133.3, 128.3, 128.2, 122.1, 122.0, 109.7, 107.5, 103.3, 99.9, 99.6, 55.6, 55.5, 39.0, 38.9, 38.7, 27.2, 27.0, 26.8. Calculated molecular ion for $C_{26}H_{32}N_4O_7$: m/z 512.55. Found: 513.2 (M$^+$), 497.1 (M$^+$—OH).

With the purpose of making the ideas expressed in these last examples easier to understand, Scheme 2, which is included below, shows the different stages of synthesis leading to the compounds mentioned in examples 10, 11, 12, 13 and 14.

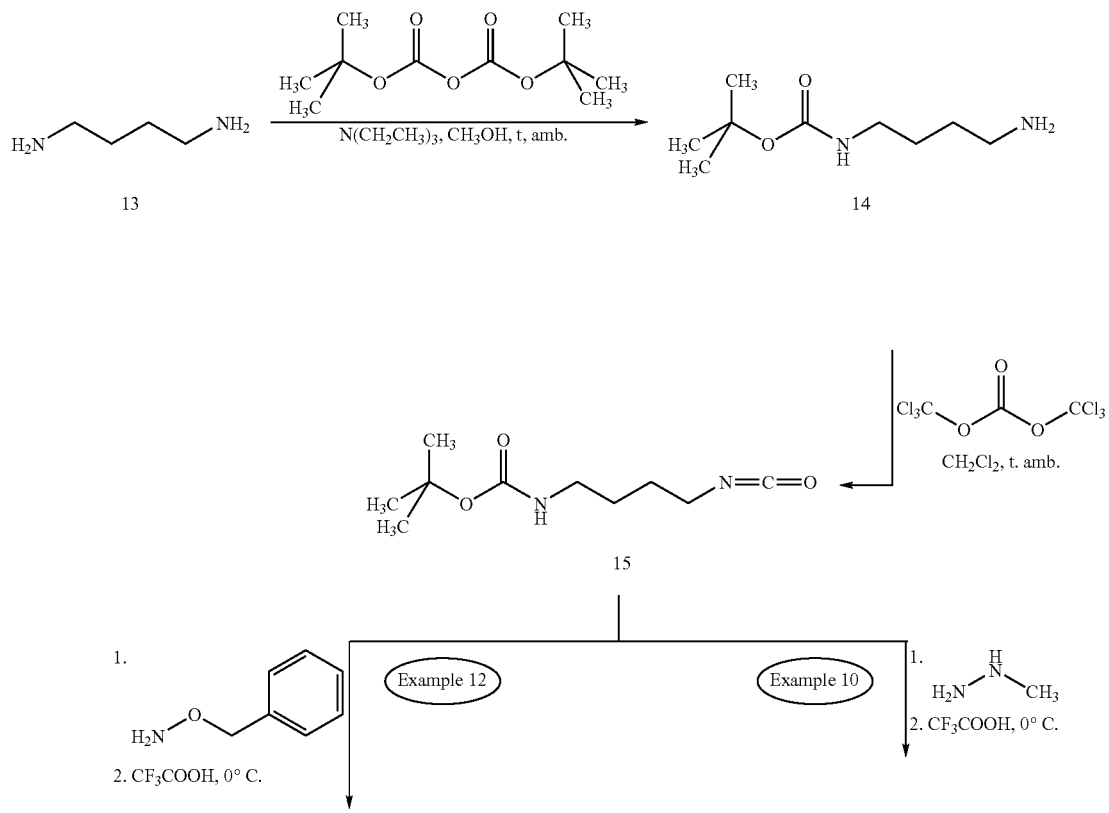

SCHEME 2

-continued
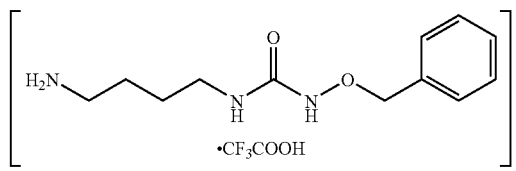
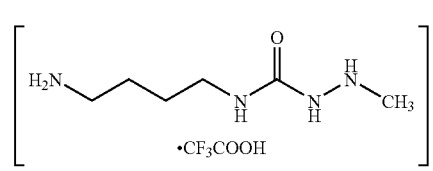
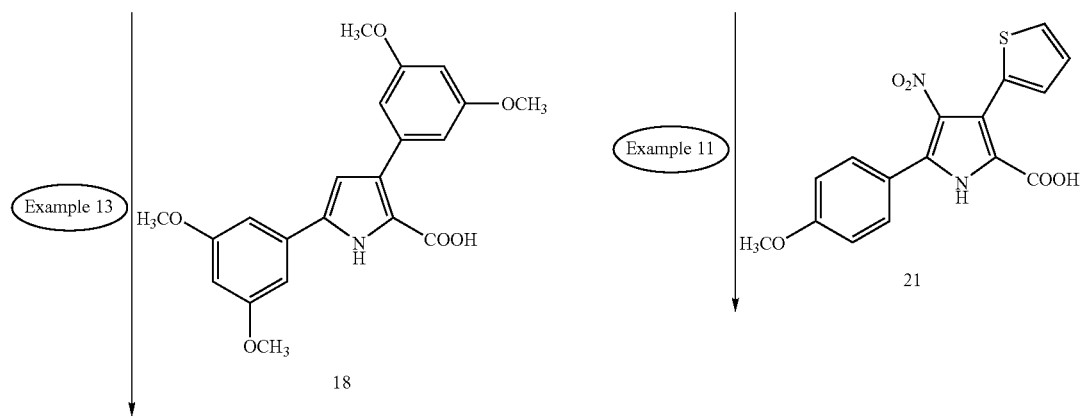
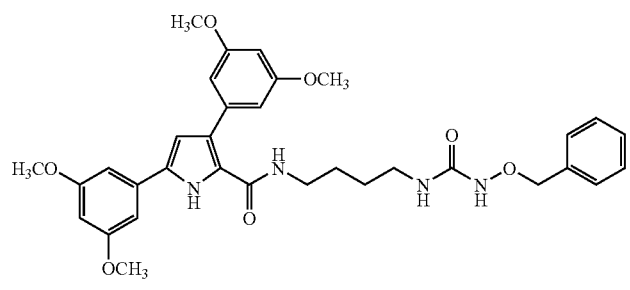
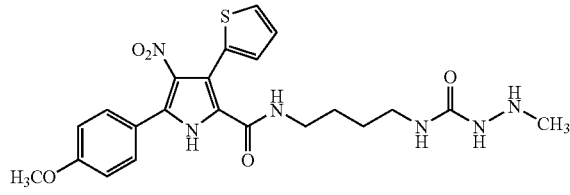
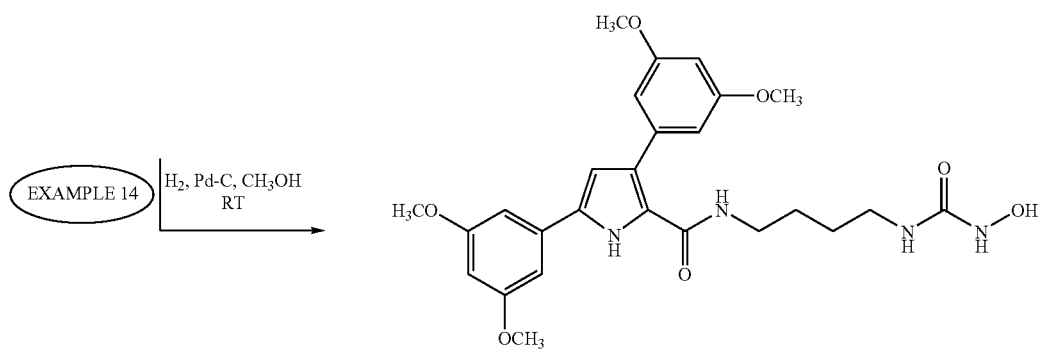

A

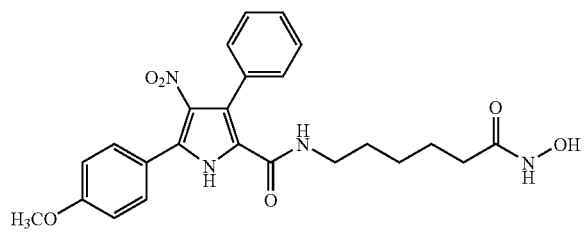

B

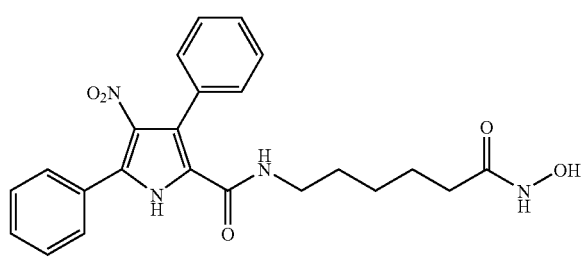

C

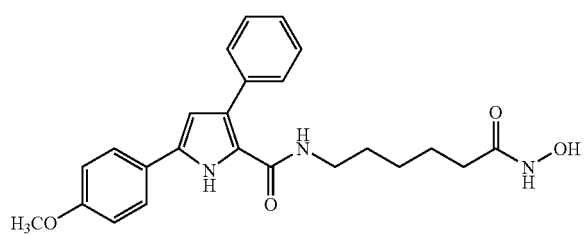

D

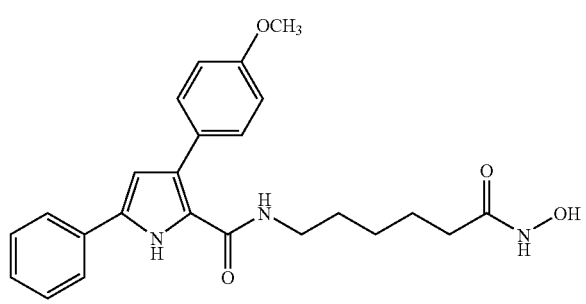

E

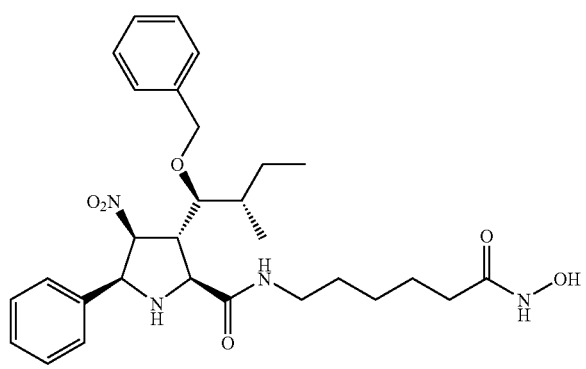

SCHEME 3. Developed formulas of the compounds whose inhibitory action is shown in FIGS. 1, 2, 3, 4, 5, 6 and 7.

Example 15

In Vitro Measurement of the Inhibitory Capacity of Histone Deacetylase Activity

With the aim of better illustrating the methods followed in the present example and in the following one the results obtained with the compounds indicated in Scheme 3, in which a derivative of a chiral pyrrolidine has been included, are given with the purpose of comparing the activity of this cyclic system with the pyrroles object of the present invention.

To determine the inhibitory capacity of the histone deacetylases of the synthesised compounds, an in vitro study was carried out by incubating the nuclear extract of cell lines HCT116 and MOLT4 and tritium labelled acetylated histones, in different concentrations of the synthesised compounds, after which the concentration of liberated acetyl groups were measured using a scintillation counter.

Preparation of Nuclear Extract

The cells ($8 \times 10^6$) in suspension were centrifuged at 800 rpm for 5 minutes, washed with PBS and resuspended in 2 ml of buffer A (10 mM Tris pH 7.5, 15 mM KCl, 2 mM $MgCl_2$, 0.1 mM EDTA, 2 mM 2-mercaptoethanol, 1 tablet of EDTA-free protease inhibitor for every 50 ml of buffer). 135 μl of buffer B (50 mM Tris, 1 M KCl, 30 mM $MgCl_2$, 0.1 mM EDTA, 2 mM 2-mercaptoethanol) was added, they were then centrifuged at $2.7 \times 10^3$ rpm at 4° C. for 5 minutes and the supernatant removed. The pellet was resuspended in 2 ml of buffer A and stirred 5 times in a 2 ml homogeniser. It was centrifuged again at $7.8 \times 10^3$ rpm at 4° C. for 8 minutes, the pellet was resuspended in 2 ml of buffer A, and stirred 5 times in the homogeniser. 200 μl ammonium sulphate was added to it and then mixed for 30 minutes on a rotary mixer at 4° C. It was centrifuged at $12 \times 10^3$ rpm at 4° C. for 10 minutes and the supernatant was dialysed in a MWCO 3500 membrane for 2 h at 4° C. in 200 ml of buffer C (20 mM Tris pH 7.5, 10% glycerol, 1 mM EDTA, 1 mM 2-mercaptoethanol, 1.5 mM $MgCl_2$, 1 tablet of EDTA-free protease inhibitor for every 50 ml of buffer). After this time, the contents of the membrane were recovered and were used for the study which is described below.

In Vitro Measurement of the Inhibitory Activity of the Compounds.

To 30 μl of the nuclear extract obtained using the method shown, 55 μl of buffer C (see above), 5 μl of the corresponding inhibitor solution and 10 μl tritium labelled hyperacetylated histones were added, and the resulting mixture was incubated at 37° C. for 1 h.

The incubation was stopped by the addition of 37.5 μl of a solution of hydrochloric acid (final concentration, 1 M) and acetic acid (final concentration, 0.4 M). 700 μl of ethyl acetate were added to the resulting mixture, it was centrifuged at 10,000 rpm for 5 minutes and, finally, the upper phase (which contained the liberated tritiated acetic acid) was used for scintillation counting. The samples for the scintillation counter were prepared by mixing 500 μl of the upper phase and 5 ml of scintillation fluid.

Figure 2:
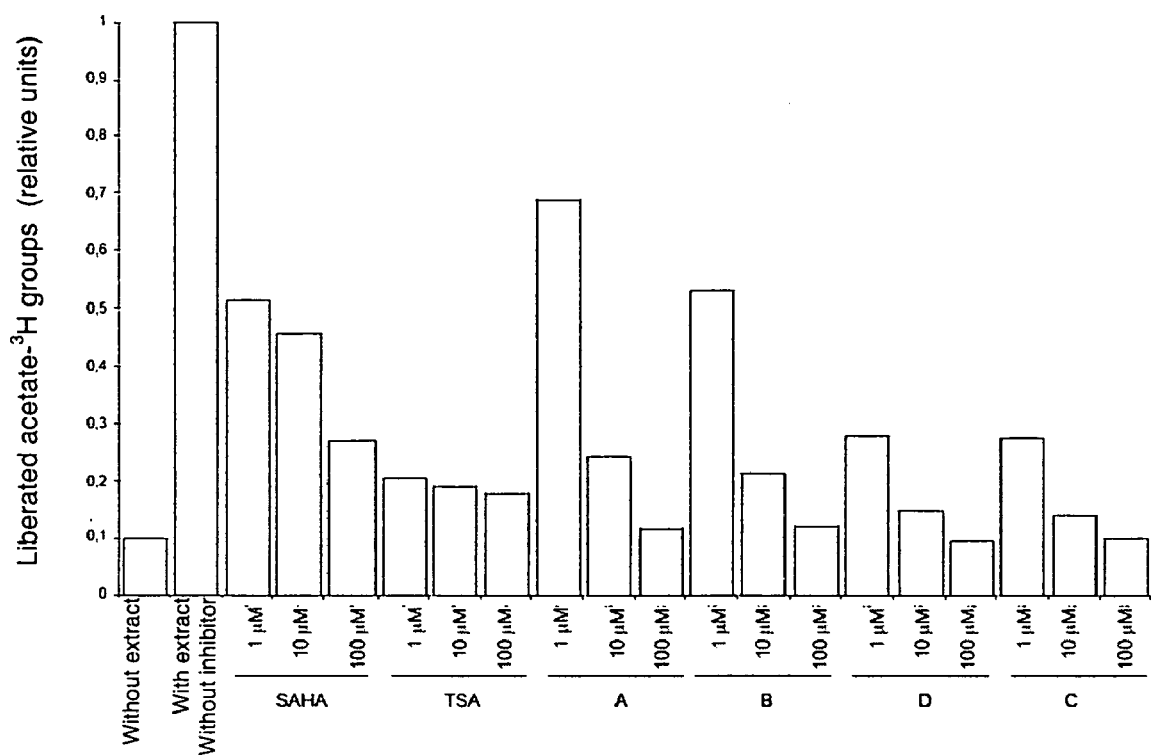
FIG. 2 shows the effect in vitro of representative examples of the compounds object of the present invention on the deacetylase activity of histones of the cell line MOLT4 (human fibroblastic leukaemia), compared with TSA and SAHA used as a positive control.

The most representative data obtained after following the previous method are shown in FIGS. 1 and 2. The results in FIG. 1 correspond to the cell line HCT116 and those of FIG. 2 correspond to the cell line MOLT4.

Example 16

Measurement of the Total Scintillation of the Histones

The quantification of the degree of acetylation of the H3 and H4 histones was carried out using the method which is described below.

Jurkat human cell lines (promyelocytic leukaemia) were treated for 24 h with different concentrations of HDAC inhibitory compounds object of the present invention. After this time, the nuclei were isolated by adding, RSB buffer (Tris 10 mM pH 7.5, 10 mM sodium chloride and 3 mM magnesium chloride) with 1% Nonidet-P40 and protease inhibitor, to the cells. To extract the histones, 0.25 M hydrochloric acid was added to nuclei, and the mixture was stirred for 16 h at 4° C. Next, the histones were precipitated by adding 8 volumes of acetone. The histone mixture obtained was separated using reverse phase high performance liquid chromatography (HPLC), using a C18 column with a acetonitrile gradient (20-60%) in 0.3% trifluoroacetic acid.

The separation of the non-acetylated, mono-, di-, tri-, and tetra-acetylated species of each fraction of the H3 and H4 histones was carried out using high performance capillary electrophoresis (HPCE), using a silica capillary (60.2 cm×75 μm, effective length 50 cm). The elution conditions used were: 25° C., voltage 12 kV, absorbance detector at 214 nm, and an elution buffer of 110 mM phosphate (pH 2.0) and HPM cellulose (0.03% wt/vol).

Before each injection, the system was washed for 3 minutes with 0.1M NaOH, followed by another wash with 0.5 M $H_2SO_4$ for 2 minutes, and it was equilibrated with the elution buffer for 3 minutes. The washing buffers and solutions were prepared with Milli-Q water filtered through a pore size of 0.45 μm. The samples were injected under a pressure of 0.3 psi for 3 seconds. All the samples were analysed in duplicate.

Figure 3:
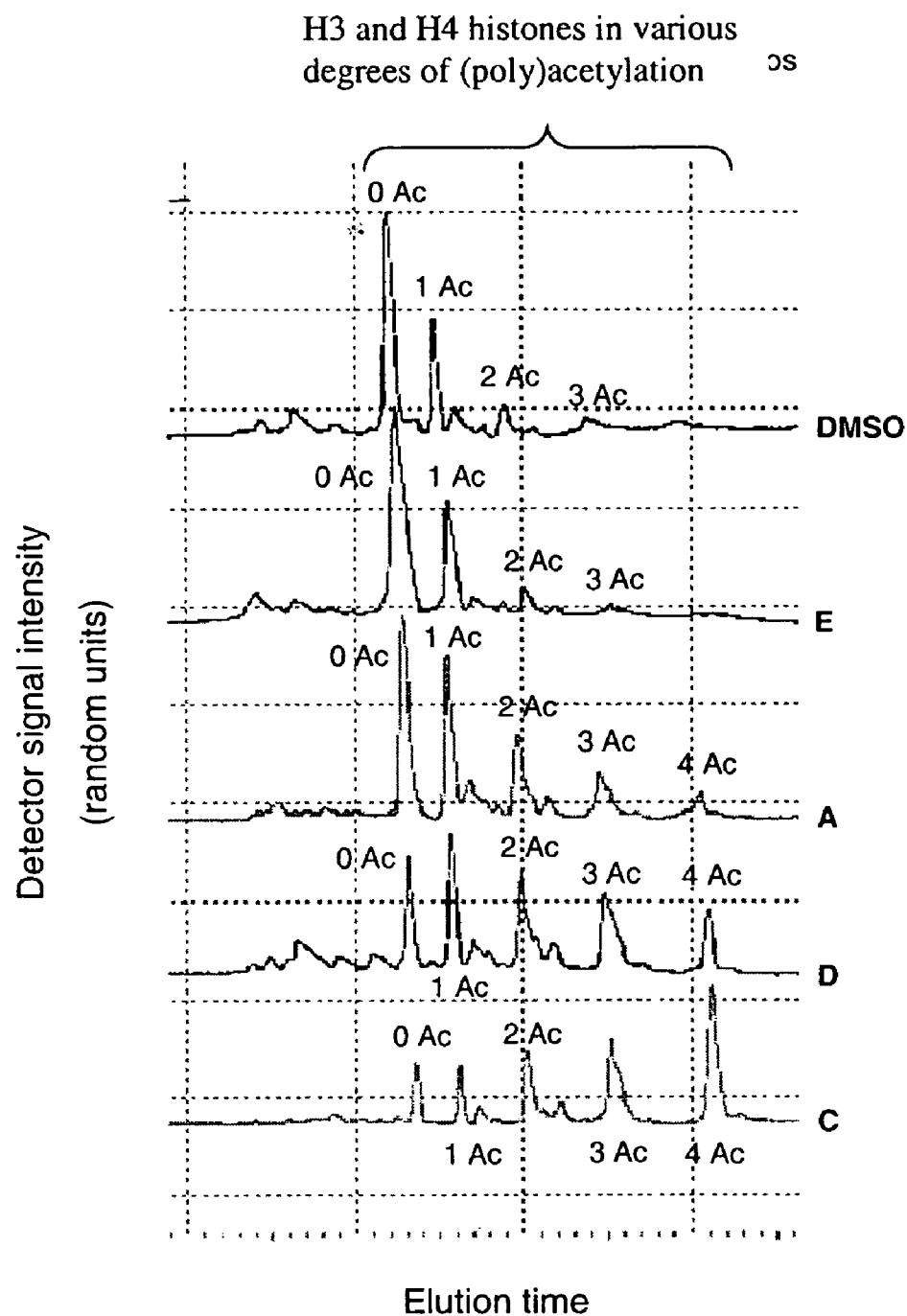
FIG. 3 shows the quantification of the level of acetylation, using HPCE (high performance capillary electrophoresis), of the H3 and H4 histones of the Jurkat human promyelocytic leukaemia cell line treated with some compounds object of the present invention at a concentration of 10 µM.

Some representative data obtained with various molecules object of the present invention are shown in FIG. 3.

Example 17

Measurement of Apoptosis Induction

The quantification of the amount of apoptotic cells was carried out by studying the change in the permeability of the cytoplasmic membrane using flow cytometric analysis, using the commercial YoPro© kit as staining agent. The method followed is explained next. The cells of human lines HCT116 and HL60 ($10^6$ cells per treatment) were treated with different concentrations of HDAC inhibitor compounds, object of the present invention, for 24 h. After this period, the cells were washed twice with cold PBS 1×, they were resuspended in 1 ml of PBS 1× and 1 μl of YoPro© and 1 μl of propidium iodide were added. The mixture was incubated protected from light for 30 minutes in ice. The quantity of apoptotic cells were measured using flow cytometry.

Figure 4:
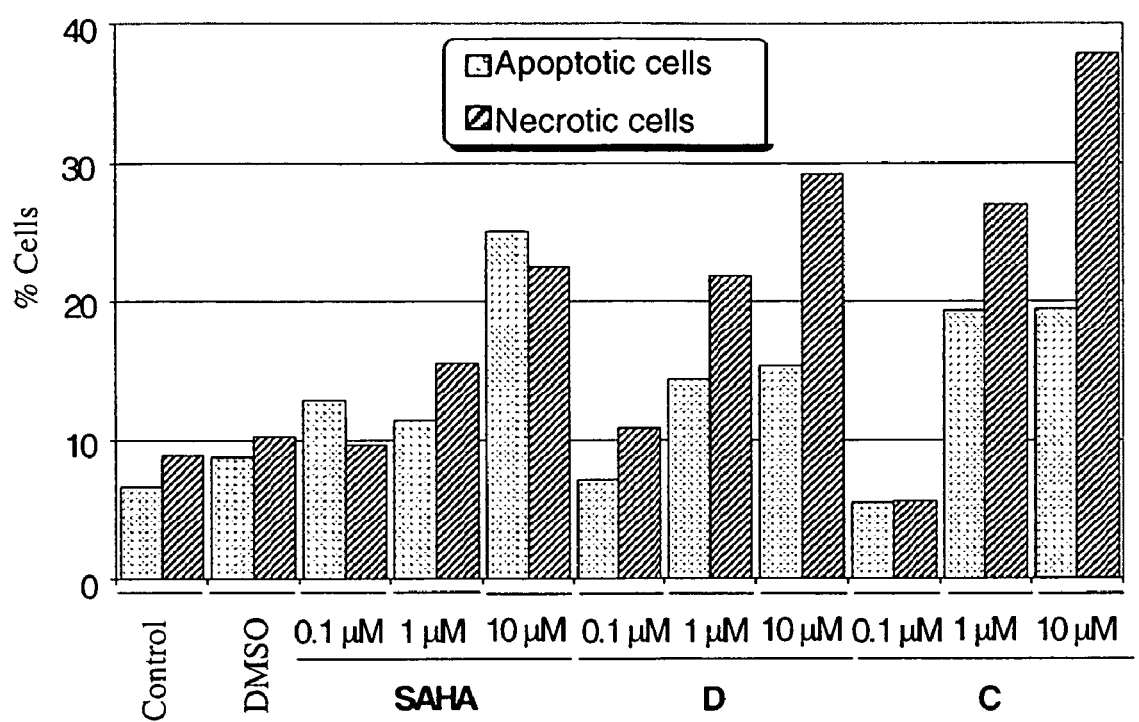
FIG. 4 shows the measurement of the percentage of apoptotic and necrotic cells in the presence of different concentrations of SAHA and two inhibitors object of the present invention. The data obtained on the control sample and on a sample treated with DMSO are also included. The data shown correspond to the human colon carcinoma model HCT116.
Figure 5:
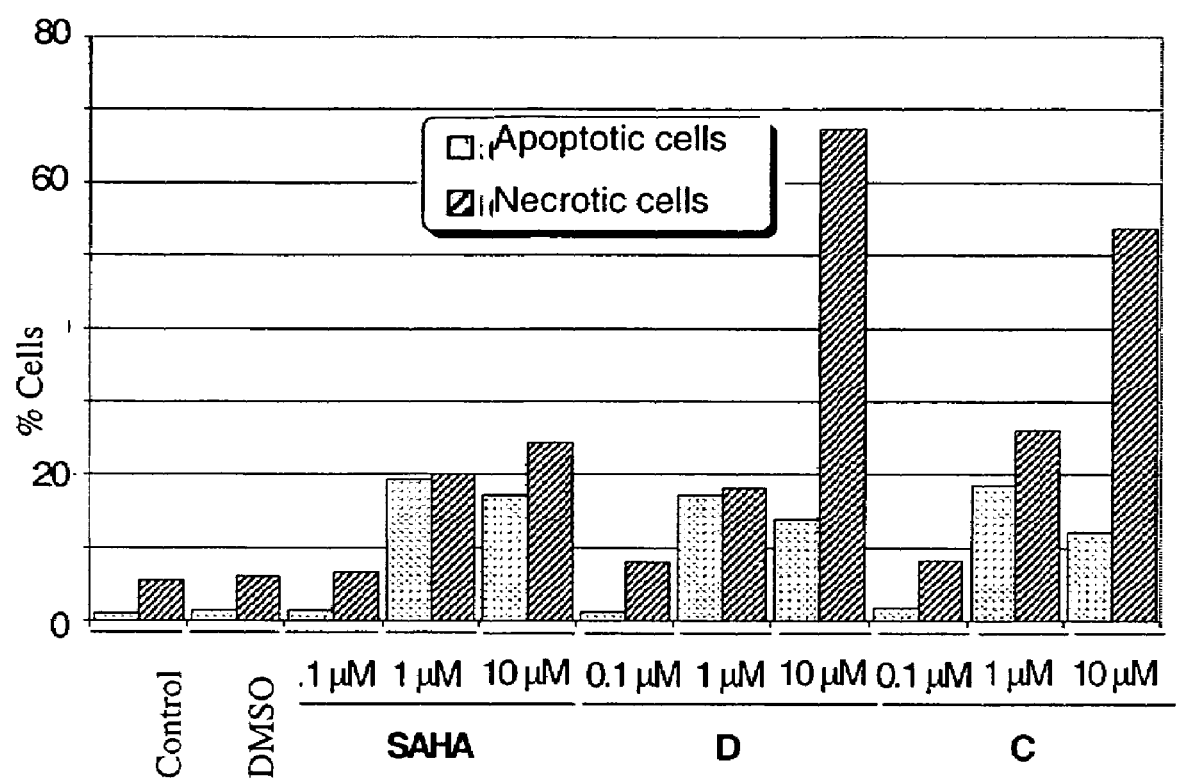
FIG. 5 shows the measurement of the percentage of apoptotic and necrotic cells in the presence of different concentrations of SAHA and two inhibitors object of the present invention. The data obtained on the control sample and on a sample treated with DMSO are also included. The data shown correspond to the human acute myeloid leukaemia model HL60.

The most representative data are shown in FIGS. 4 and 5. The data relevant to the human carcinoma of the colon HCT116 model are represented in FIG. 4. The data relevant to human acute myeloid leukaemia HL60 model are represented in FIG. 5.

Example 18

Measurement of In Vivo Biological Activity

With the aim of observing the effect of some of the compounds described on tumour growth in vivo, studies were carried out using 6 week old female athymic nude mice (Harlam Sprague Dawley, Indianapolis, Ind., USA). For the study $2×10^6$ cells of line HCT116 (human colon carcinoma) and $10^7$ MOLT4 cells (human T cell acute lymphoblastic leukaemia) were inoculated subcutaneously in a final inoculation volume of 200 μl/animal resuspended in PBS. When the tumours reached a mean volume of 100 $mm^3$, each mouse was administered a daily dose of 200 μl of 20 μM solution of the corresponding molecule by intraperitoneal injection (10 mg/kg weight). The control group of mice were administered 200 μl of PBS to mimic the stress of the inoculation. The mice were weighed every 24 h, and the tumour volume was measured using a calibrated millimeter measuring device, assuming a spherical geometry for the tumours (volume=$d^3×π/6$). When the tumours reached a volume of 1-1.5 $cm^3$ (Ethical-Humanitarian Human End Point), the mice were sacrificed and the tumours were extracted and weighed.

Figure 6:
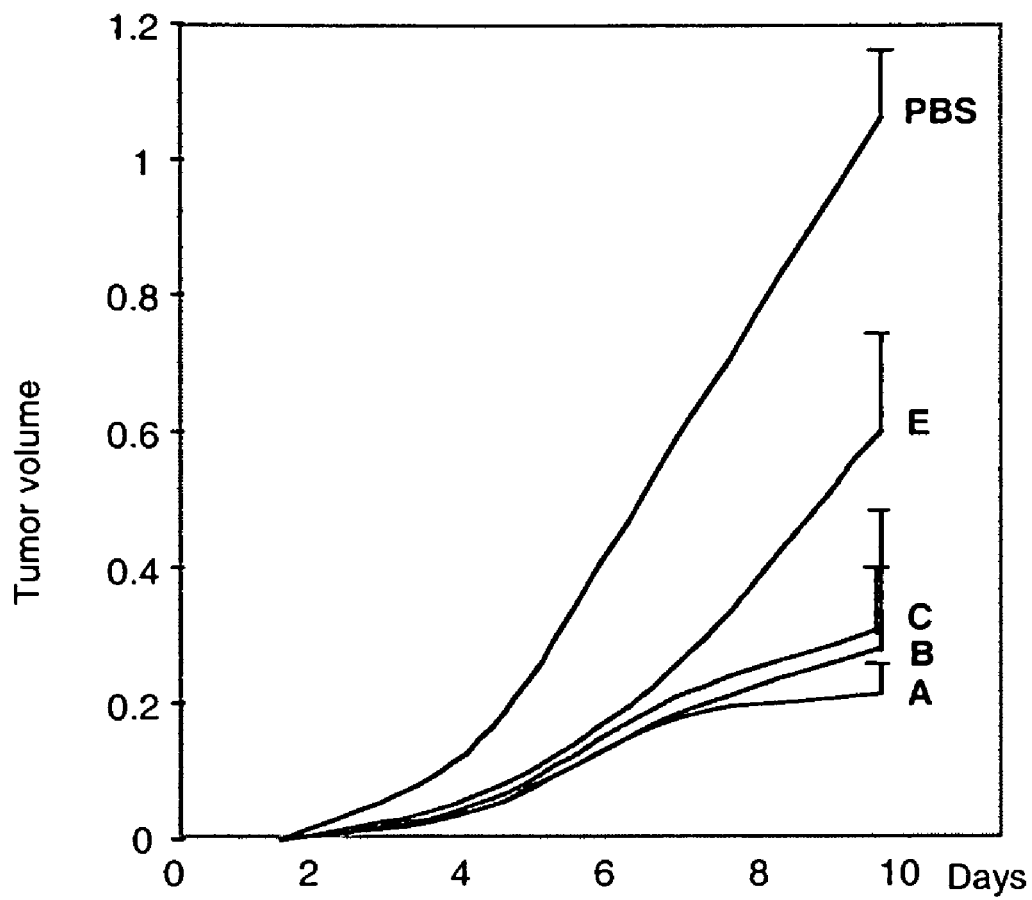
FIG. 6 shows the inhibition of tumour growth of human colon carcinoma HCT116 in athymic nude mice, caused by the intraperitoneal administration of some of the compounds object of the present invention. The xeno-implants were performed intrasplenically and the inhibitors were injected intraperitoneally, according to the method detailed in example No. 18.
Figure 6:
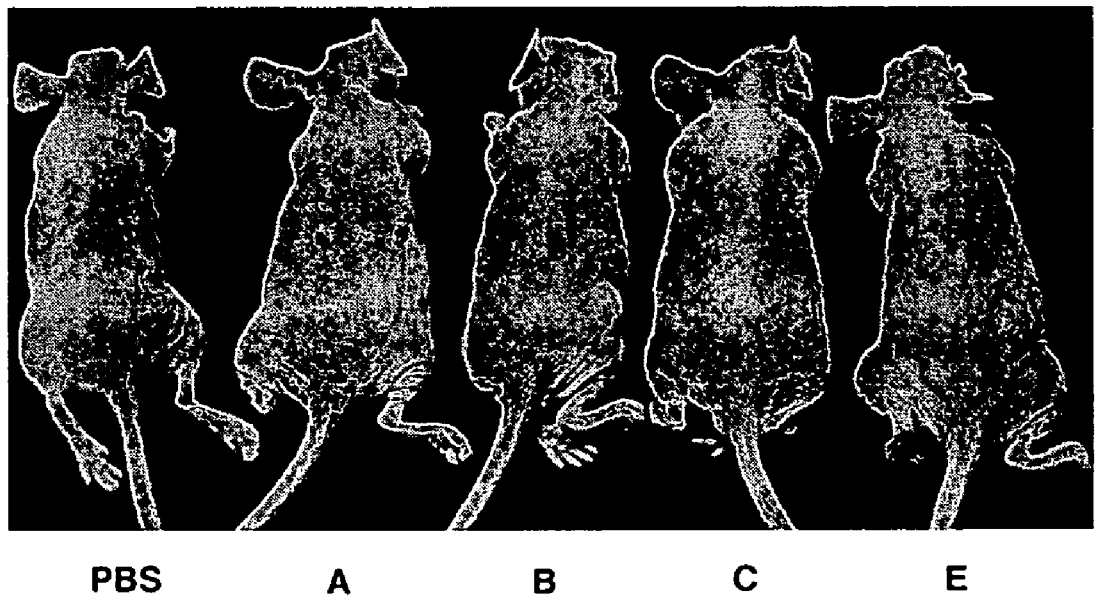
Figure 7:
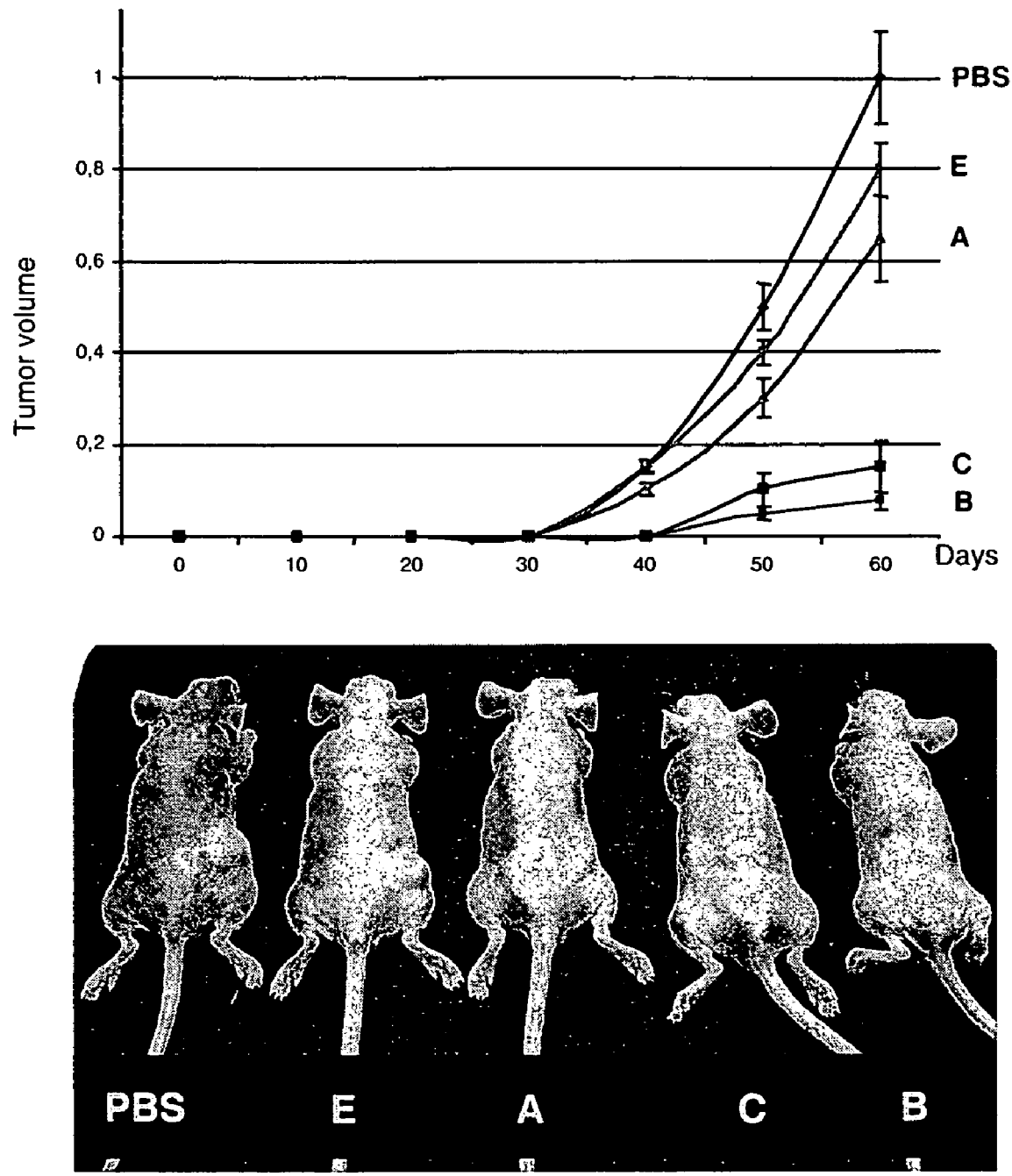
FIG. 7 shows in vivo anti-tumoural activity in athymic nude mice of some of the compounds object of the present invention in the human fibroblastic leukaemia model MOLT4. The xeno-implants were performed intrasplenically according to the method detailed in example No. 17.

The most representative data are shown in FIGS. 6 and 7. The data regarding the human colon carcinoma HCT 116 model are presented in FIG. 6. In FIG. 7 the data relative to the human fibroblastic leukaemia MOLT4 model are presented.

The invention claimed is:
1. A pyrrole derivative of general formula I,

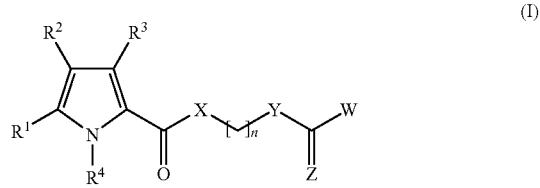

(I)

where:
$R^1$ and $R^3$ each represent, independently, a substituent selected from the group consisting of a phenyl radical; mono- or polysubstituted phenyl in different positions on the ring; and a C5-C10 heteroaryl group which contains at least one heteroatom selected from the group consisting of O, N and S;
$R^2$ is selected from the group consisting of a hydrogen atom, an electron attractor group, an amino group and an amide group;
$R^4$ represents a hydrogen atom or a linear, branched or cyclic C1-C6 alkyl group;
(n) represents a number of methylene groups between 1 and 8, both inclusive;
(X) represents either a secondary amine group, an oxygen atom or a sulphur atom;
(Y) is selected from the group consisting of a methylene group, a substituted methylene group and a secondary amine group;
(Z) represents either an oxygen atom or a sulphur atom; and
(W) is selected from the group consisting of hydroxyl, hydroxyamine, hydrazine, alkyl, aryl and heteroaryl-hydrazine.

2. The pyrrole derivative of general formula I in accordance with claim 1 selected from:

[1] 6(3,5-diphenyl-1H-pyrrole-2-carboxamide)hexanoic acid, with the following structural formula:

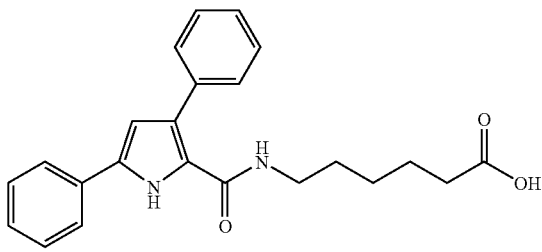

[2] 6-(4-nitro-3,5-diphenyl-1H-pyrrole-2-carboxamide) hexanoic acid, with the following structural formula:

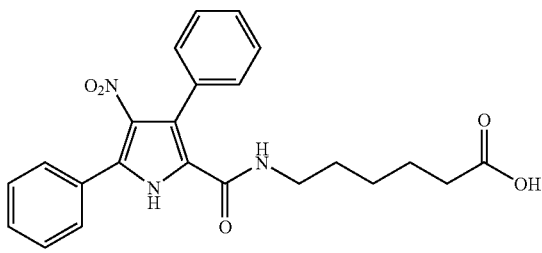

[3] N-(5-(Hydroxycarbamoyl)pentyl)-5-phenyl-3-(4-methoxyphenyl)-1H-pyrrole-2-carboxamide, with the following structural formula:

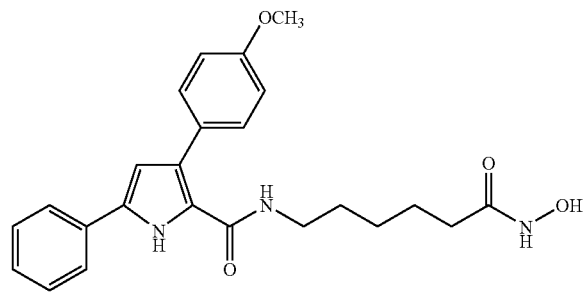

[4] N-(5-(Hydroxycarbamoyl)pentyl)-3-phenyl-5-(4-methoxyphenyl)-1H-pyrrole-2-carboxamide, with the following structural formula:

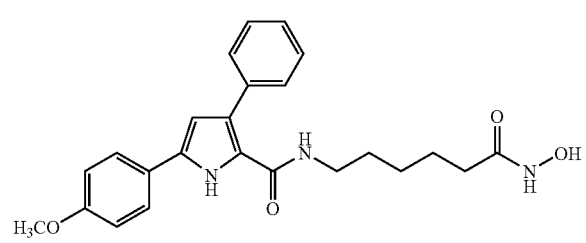

[5] N-(5-(Hydroxycarbamoyl)pentyl)-3-phenyl-5-(4-methoxyphenyl)-4-nitro-1H-pyrrole-2-carboxamide, with the following structural formula:

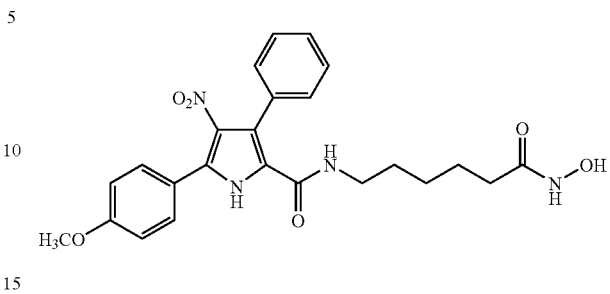

[6] 1-(4-(3,5-bis(3,5-Dimethoxyphenyl)-1H-pyrrole-2-carboxamide)butyl)-3-hydroxyurea, with the following structural formula:

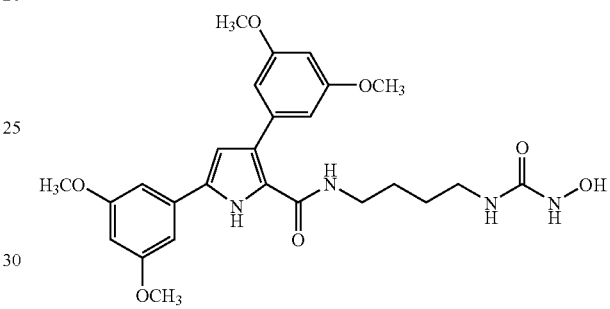

[7] 1-(4-(5-(4-Methoxyphenyl)-4-nitro-3-(thiophen-2-yl)-1H-pyrrole-2-carboxamide)butyl)-3-(2-methylamine) urea, with the following structural formula:

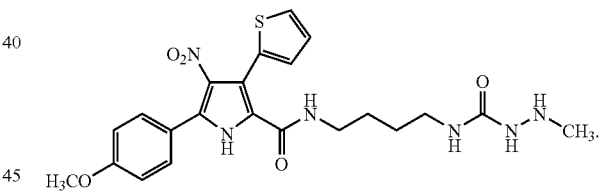

3. A Process for the preparation of compounds of general formula (Ia):

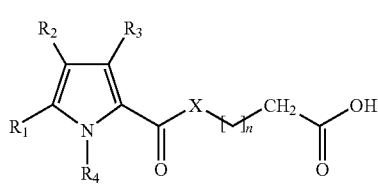

(Ia)

where:

$R_1$ and $R_3$ each represent, independently, a substituent selected from the group consisting of a phenyl radical; mono- or polysubstituted phenyl in different positions on the ring; and a C5-C10 heteroaryl group which contains at least one heteroatom selected from the group consisting of O, N and S:

R$_2$ is selected from the group consisting of a hydrogen atom, an electron attractor group, an amino group and an amide group;

R$_4$ represents a hydrogen atom or a linear, branched or cyclic C1-C6 alkyl group;

(n) represents a number of methylene groups between 1 and 8, both inclusive; and (X) represents either a secondary amine group, an oxygen atom or a sulphur atom;

which process comprises reacting a mixture comprised of:

a) A 1H-pyrrole-2-carboxylic acid of formula II,

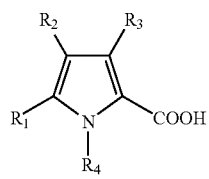

(II)

b) A compound of formula III,

 (III)

where R$^5$ is an alkoxycarbonyl, c) A reagent capable of activating the carboxyl group; and d) A tertiary amine, selected from the group consisting of cyclic and acyclic aliphatics with C3-C10 carbons and alkane aromatics with C9-C15 carbons, and reacting a product thus obtained with a mixture comprising lithium or sodium hydroxide, dimethoxyethane and water.

4. A process for the preparation of compounds of general formula (Ib):

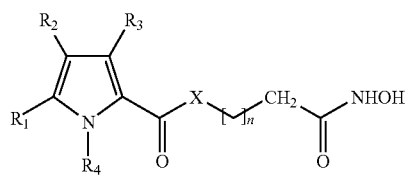

(Ib)

where:

R$_1$ and R$_3$ each represent, independently, a substituent selected from the group consisting of a phenyl radical; mono- or polysubstituted phenyl in different positions on the ring; and a C5-C10 heteroaryl group which contains at least one heteroatom selected from the group consisting of O, N and S;

R$_2$ is selected from the group consisting of a hydrogen atom, an electron attractor group, an amino group and an amide group;

R$_4$ represents a hydrogen atom or a linear, branched or cyclic C1-C6 alkyl group;

(n) represents a number of methylene groups between 1 and 8, both inclusive; and (X) represents either a secondary amine group, an oxygen atom or a sulphur atom;

which process comprises reacting a mixture comprised of:

a) A 1H-pyrrole-2-carboxylic acid of formula II,

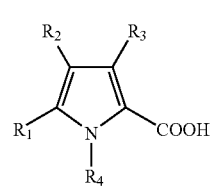

(II)

b) A compound of formula III,

 (III)

where R$^5$ is a alkoxycarbonyl, c) A reagent for the activation of the carboxyl group; and d) A tertiary amine, selected from the group consisting of cyclic and acyclic aliphatics with C3-C10 carbons and alkane aromatics with C9-C15 carbons, and adding a resulting product to a mixture of hydroxylamine chlorhydrate and phenolphthalein in the presence of an excess of sodium methoxide in methanol.

5. A process for the preparation of compounds of general formula (Ic):

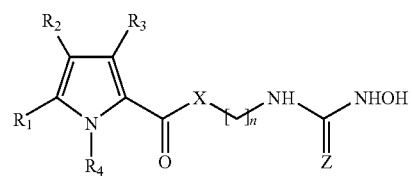

where:

R$_1$ and R$_3$ each represent, independently, a substituent selected from the group consisting of a phenyl radical; mono- or polysubstituted phenyl in different positions on the ring; and a C5-C10 heteroaryl group which contains at least one heteroatom selected from the group consisting of O, N and S;

R$_2$ is selected from the group consisting of a hydrogen atom, an electron attractor group, an amino group and an amide group;

R$_4$ represents a hydrogen atom or a linear, branched or cyclic C1-C6 alkyl group;

(n) represents a number of methylene groups between 1 and 8, both inclusive;

(X) represents either a secondary amine group, an oxygen atom or a sulphur atom; and (Z) represents either an oxygen or sulphur atom;

which process comprises reacting a mixture comprising:

a) A 1H-pyrrole-2-carboxylic acid of formula II,

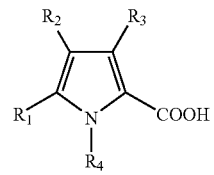

(II)

b) A compound of formula III,

 (III)

where R⁵ is t-butoxycarbamoyl (NHBoc) or benzyloxycarbamoyl (NHCBz),
  c) A reagent capable of activating the carboxyl group; and
  d) A tertiary amine, selected from the group consisting of cyclic and acyclic aliphatics with C3-C10 carbons and alkane aromatics with C9-C15 carbons,
to unprotect a product obtained by means of acid treatment or hydrolysis; and reacting said unprotected product with phosgene or one of its analogues so as to obtain an isocyanate which is treated with hydroxylamine.

6. A process for the preparation of compounds of general formula (Id):

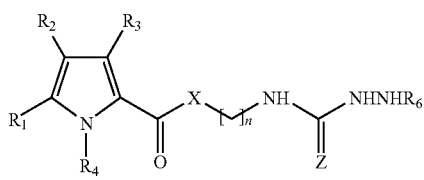

where:
  $R_1$ and $R_3$ each represent, independently, a substituent selected from the group consisting of a phenyl radical; mono- or polysubstituted phenyl in different positions on the ring; and a C5-C10 heteroaryl group which contains at least one heteroatom selected from the group consisting of O, N and S;
  $R_2$ is selected from the group consisting of a hydrogen atom, an electron attractor group, an amino group and an amide group;
  $R_4$ represents a hydrogen atom or a linear, branched or cyclic C1-C6 alkyl group;
  (n) represents a number of methylene groups between 1 and 8, both inclusive;
  (X) represents either a secondary amine group, an oxygen atom or a sulphur atom; and
  (Z) represents either an oxygen or sulphur atom;
and $R_6$ is a H, C1-C6 alkyl, aryl or heteroaryl of 5 or 6 members with 1 or more heteroatoms selected from the group consisting of O, N and S, which process comprises reacting a mixture comprising:
  a) A 1H-pyrrole-2-carboxylic acid of formula II,

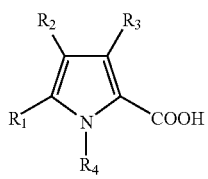

b) A compound of formula III,

HX—(CH$_2$)$_n$—R⁵    (III)

where R⁵ is t-butoxycarbamoyl (NHBoc) or benzyloxycarbamoyl (NHCBz),
  c) A reagent capable of activating the carboxyl group; and
  d) A tertiary amine, selected from the group consisting of cyclic or acyclic aliphatics with C3-C10 carbons and alkane aromatics with C9-C15 carbons, to unprotect a product obtained by means of acid treatment or hydrogenolysis and reacting the unprotected product with phosgene or its analogues so as to obtain an isocyanate or thioisocyanate which is treated with a substituent selected from the group consisting of hydrazine and alkyl, aryl and heteroaryl-hydrazines.

7. A process for the preparation of compounds of general formula (Id):

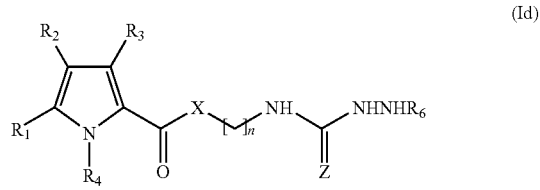

where:
  $R_1$ and $R_3$ each represent, independently, a substituent selected from the group consisting of a phenyl radical; mono- or polysubstituted phenyl in different positions on the ring; and a C5-C10 heteroaryl group which contains at least one heteroatom selected from the group consisting of O, N and S;
  $R_2$ is selected from the group consisting of a hydrogen atom, an electron attractor group, an amino group and an amide group;
  $R_4$ represents a hydrogen atom or a linear, branched or cyclic C1-C6 alkyl group;
  (n) represents a number of methylene groups between 1 and 8, both inclusive;
  (X) represents either a secondary amine group, an oxygen atom or a sulphur atom; and
  (Z) represents either an oxygen or sulphur atom;
and $R_6$ is a H, C1-C6 alkyl, aryl or heteroaryl of 5 or 6 members with 1 or more heteroatoms selected between from the group consisting of O, N and S, which process comprises reacting a mixture comprising:
  a) A 1H-pyrrole-2-carboxylic acid of formula II,

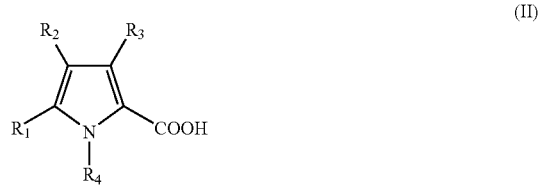

b) A compound of formula III,

HX—(CH$_2$)$_n$—R⁵    (III)

where R⁵ is 3-benzyloxyureyl or 3-alkyl, aryl or heteroaryl ureyl,
  c) A reagent capable of activating the carboxyl group; and
  d) A tertiary amine, selected from the group consisting of cyclic and acyclic aliphatics with C3-C10 carbons and alkane aromatics with C9-C15 carbons.

8. A method of treating colon carcinoma, acute myeloid leukemia, and human fibroblastic leukemia in a subject in need thereof, which method comprises administering to said subject a therapeutically effective amount of a pyrrole derivative in accordance with claim 1.

9. A method of treating colon carcinoma, acute myeloid leukemia, and human fibroblastic leukemia in a subject in need thereof, which method comprises administering to said subject a therapeutically effective amount of a pyrrole derivative in accordance with claim 2.

10. A method for manufacturing a medicament for the treatment of colon carcinoma, acute myeloid leukemia, and human fibroblastic leukemia which comprises including within said medicament a therapeutically effective amount of a pyrrole derivative in accordance with claim 1.

11. A method for manufacturing a medicament for the treatment of colon carcinoma, acute myeloid leukemia, and human fibroblastic leukemia which comprises including within said medicament a therapeutically effective amount of a pyrrole derivative in accordance with claim 2.

12. A pharmaceutical composition comprising a pyrrole derivative in accordance with claim 1 and a pharmaceutically acceptable excipient.

13. A pharmaceutical composition comprising a pyrrole derivative in accordance with claim 2 and a pharmaceutically acceptable excipient.

14. The pyrrole derivative of general formula (I), in accordance with claim 1, wherein $R_2$ is a nitro group.

15. The process of claim 3 wherein, in the pyrrole derivative of general formula (Ia), $R_2$ is a nitro group.

16. The process of claim 4 wherein, in the pyrrole derivative of general formula (II), $R_2$ is a nitro group.

17. The process of claim 5 wherein, in the pyrrole derivative of general formula (Ic), $R_2$ is a nitro group.

18. The process of claim 6 wherein, in the pyrrole derivative of general formula (Id), $R_2$ is a nitro group.

19. The process of claim 6, wherein the analogue of phosgene is selected from the group consisting of diphosgene, triphosgene and thiophosgene.

20. The process of claim 7 wherein, in the pyrrole derivative of general formula (Id), $R_2$ is a nitro group.

* * * * *

UNITED STATES PATENT AND TRADEMARK OFFICE
CERTIFICATE OF CORRECTION

PATENT NO. : 7,638,550 B2  Page 1 of 1
APPLICATION NO. : 10/571497
DATED : December 29, 2009
INVENTOR(S) : Cossio Mora et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 950 days.

Signed and Sealed this

Ninth Day of November, 2010

David J. Kappos
*Director of the United States Patent and Trademark Office*